US012576251B2

(12) United States Patent
Hedstrom et al.

(10) Patent No.: US 12,576,251 B2
(45) Date of Patent: Mar. 17, 2026

(54) SYSTEMS AND METHODS FOR THE CONDITIONING OF CEREBROSPINAL FLUID

(71) Applicant: MINNETRONIX NEURO, INC., Excelsior, MN (US)

(72) Inventors: Blake Hedstrom, Minneapolis, MN (US); Shivanand P. Lad, Durham, NC (US); Aaron McCabe, Edina, MN (US); Emily Meyering, St. Louis Park, MN (US); Jack Mondry, Edina, MN (US); Amrita Sawhney, Princeton Junction, NJ (US); Elizabeth Scheurer, Minneapolis, MN (US); Matthew Stoll, Minneapolis, MN (US); Abhi Vase, Los Altos Hills, CA (US)

(73) Assignee: PHARAOH NEURO, INC., Minneapolis, MN (US)

( * ) Notice: Subject to any disclaimer, the term of this patent is extended or adjusted under 35 U.S.C. 154(b) by 597 days.

(21) Appl. No.: 18/105,668

(22) Filed: Feb. 3, 2023

(65) Prior Publication Data

US 2023/0181883 A1     Jun. 15, 2023

Related U.S. Application Data

(63) Continuation of application No. 16/742,870, filed on Jan. 14, 2020, now Pat. No. 11,577,060, which is a
(Continued)

(51) Int. Cl.
A61M 27/00 (2006.01)
A61M 25/00 (2006.01)

(52) U.S. Cl.
CPC ... A61M 27/006 (2013.01); A61M 2025/0031 (2013.01); A61M 2205/053 (2013.01);
(Continued)

(58) Field of Classification Search
CPC ........ A61M 27/006; A61M 2025/0031; A61M 2205/053; A61M 2205/054;
(Continued)

(56) References Cited

U.S. PATENT DOCUMENTS

| 2,969,066 A | 1/1961 | Holter et al. |
| 3,419,010 A | 12/1968 | Williamson |
| | (Continued) | |

FOREIGN PATENT DOCUMENTS

| CA | 2407214 A1 | 4/2003 |
| CA | 2597293 A1 | 8/2006 |
| | (Continued) | |

OTHER PUBLICATIONS

Park et al; "Continuous Dielectrophoretic Bacterial Separation and Concentration from Physiological Media of High Conductivity," The Royal Society of Chemistry, Lab Chip, vol. 11, pp. 2893-2900, 2011.
(Continued)

*Primary Examiner* — Susan S Su
*Assistant Examiner* — Erin A Kim
(74) *Attorney, Agent, or Firm* — Seager, Tufte & Wickhem LLP

(57) ABSTRACT

Systems and methods for treating biologic fluids are disclosed. Some disclosed embodiments may be used to filter cerebrospinal fluid (CSF) from a human or animal subject, heat CSF to a target temperature, cool CSF to a target temperature, apply light treatment to CSF, separate cells via their dielectric properties, apply spiral and/or centrifugal separation, introduce additives to target particles, and/or apply combinations thereof. The method may include the steps of withdrawing fluid comprising CSF, treating the fluid, and returning a portion of the treated fluid to the
(Continued)

subject. During operation of the system, various parameters may be modified, such as flow rate.

20 Claims, 10 Drawing Sheets

Related U.S. Application Data continuation of application No. 15/367,592, filed on Dec. 2, 2016, now Pat. No. 10,695,545.

(60) Provisional application No. 62/263,305, filed on Dec. 4, 2015.

(52) U.S. Cl.
CPC .................. *A61M 2205/054* (2013.01); *A61M 2205/3344* (2013.01); *A61M 2205/36* (2013.01); *A61M 2205/50* (2013.01); *A61M 2205/75* (2013.01); *A61M 2230/005* (2013.01)

(58) Field of Classification Search
CPC ...... A61M 2205/3344; A61M 2205/36; A61M 2205/50; A61M 2205/75; A61M 2230/005; A61M 2027/004; A61M 2202/0464
See application file for complete search history.

(56) References Cited

U.S. PATENT DOCUMENTS

| | | | |
|---|---|---|---|
| 3,867,937 A | 2/1975 | Schwartz | |
| 3,889,687 A | 6/1975 | Harris et al. | |
| 4,378,797 A | 4/1983 | Osterholm | |
| 4,446,154 A | 5/1984 | Osterholm | |
| 4,451,251 A | 5/1984 | Osterholm | |
| 4,551,137 A | 11/1985 | Osborne | |
| 4,686,085 A | 8/1987 | Osterholm | |
| 4,695,541 A | 9/1987 | Taylor | |
| 4,767,409 A | 8/1988 | Brooks | |
| 4,830,849 A | 5/1989 | Osterholm | |
| 4,888,115 A | 12/1989 | Marinaccio et al. | |
| 4,904,237 A * | 2/1990 | Janese | A61M 1/30 604/28 |
| 4,950,232 A | 8/1990 | Ruzicka et al. | |
| 4,958,901 A | 9/1990 | Coombs | |
| 5,160,323 A | 11/1992 | Andrew | |
| 5,171,226 A | 12/1992 | McCrory | |
| 5,190,529 A | 3/1993 | McCrory et al. | |
| 5,334,315 A | 8/1994 | Matkovich et al. | |
| 5,396,899 A | 3/1995 | Strittmatter | |
| 5,405,316 A | 4/1995 | Magram | |
| 5,423,738 A | 6/1995 | Robinson et al. | |
| 5,456,843 A | 10/1995 | Koenhen | |
| 5,462,667 A | 10/1995 | Wollinsky et al. | |
| 5,531,673 A | 7/1996 | Helenowski | |
| 5,560,828 A | 10/1996 | Wenten | |
| 5,601,727 A | 2/1997 | Bormann et al. | |
| 5,683,357 A | 11/1997 | Magram | |
| 5,726,026 A | 3/1998 | Wilding et al. | |
| 5,755,968 A | 5/1998 | Stone | |
| 5,772,607 A | 6/1998 | Magram | |
| 5,836,928 A | 11/1998 | Gerber et al. | |
| 5,897,528 A | 4/1999 | Schultz | |
| 5,941,853 A | 8/1999 | Collins | |
| 5,947,689 A | 9/1999 | Schick | |
| 5,948,441 A | 9/1999 | Lenk et al. | |
| 5,980,480 A | 11/1999 | Rubenstein et al. | |
| 6,013,051 A | 1/2000 | Nelson | |
| 6,022,742 A | 2/2000 | Kopf | |
| 6,056,725 A | 5/2000 | Elsberry | |
| 6,113,797 A | 9/2000 | Al-Samadi | |
| 6,217,552 B1 | 4/2001 | Barbut et al. | |
| 6,238,382 B1 | 5/2001 | Schock et al. | |
| 6,264,625 B1 | 7/2001 | Rubenstein et al. | |
| 6,269,699 B1 | 8/2001 | Gilman et al. | |
| 6,326,044 B1 | 12/2001 | Lindquist | |
| 6,379,331 B2 | 4/2002 | Barbut et al. | |
| 6,383,159 B1 | 5/2002 | Saul et al. | |
| 6,383,380 B1 | 5/2002 | Kopf | |
| 6,387,290 B1 | 5/2002 | Brody et al. | |
| 6,468,219 B1 | 10/2002 | Njemanze | |
| 6,537,241 B1 | 3/2003 | Odland | |
| 6,558,353 B2 | 5/2003 | Zohmann | |
| 6,575,928 B2 | 6/2003 | Saul et al. | |
| 6,594,880 B2 | 7/2003 | Elsberry | |
| 6,641,563 B1 | 11/2003 | Vitullo et al. | |
| 6,682,508 B1 | 1/2004 | Meythaler et al. | |
| 6,689,085 B1 | 2/2004 | Rubenstein et al. | |
| 6,689,756 B2 | 2/2004 | Hesson et al. | |
| 6,709,426 B2 | 3/2004 | Gijsbers et al. | |
| 6,733,675 B2 | 5/2004 | Ando et al. | |
| 6,758,832 B2 | 7/2004 | Barbut et al. | |
| 6,830,561 B2 | 12/2004 | Jansen et al. | |
| 6,849,185 B1 | 2/2005 | Wu et al. | |
| 6,875,192 B1 | 4/2005 | Saul et al. | |
| 6,969,383 B2 | 11/2005 | Hildebrand | |
| 7,011,647 B2 | 3/2006 | Purdy et al. | |
| 7,025,742 B2 | 4/2006 | Rubenstein et al. | |
| 7,108,680 B2 | 9/2006 | Rohr et al. | |
| 7,150,737 B2 | 12/2006 | Purdy et al. | |
| 7,181,289 B2 | 2/2007 | Pflueger et al. | |
| 7,189,221 B2 | 3/2007 | Silverberg et al. | |
| 7,214,211 B2 | 5/2007 | Woehr et al. | |
| 7,252,659 B2 | 8/2007 | Shehada et al. | |
| 7,318,834 B2 | 1/2008 | Njemanze | |
| 7,455,666 B2 | 11/2008 | Purdy | |
| 7,708,716 B2 | 5/2010 | Shah | |
| 7,787,954 B2 | 8/2010 | Purdy | |
| 7,842,002 B2 | 11/2010 | Mantle | |
| 7,850,723 B1 | 12/2010 | Magers | |
| 7,887,503 B2 | 2/2011 | Geiger | |
| 8,029,495 B2 | 10/2011 | Pyles | |
| 8,131,353 B2 | 3/2012 | Purdy | |
| 8,137,334 B2 | 3/2012 | Heruth et al. | |
| 8,231,586 B2 | 7/2012 | Kizer et al. | |
| 8,357,296 B2 | 1/2013 | Bonhomme et al. | |
| 8,398,581 B2 | 3/2013 | Panotopoulos | |
| 8,435,204 B2 | 5/2013 | Lad et al. | |
| 8,444,661 B2 | 5/2013 | Nair et al. | |
| 8,475,419 B2 | 7/2013 | Eckermann | |
| 8,486,023 B2 | 7/2013 | Pyles | |
| 8,486,104 B2 | 7/2013 | Samson et al. | |
| 8,512,280 B2 | 8/2013 | Rozenberg et al. | |
| 8,518,636 B2 | 8/2013 | Bosch et al. | |
| 8,523,930 B2 | 9/2013 | Saunders et al. | |
| 8,603,057 B2 | 12/2013 | Hoffman et al. | |
| 8,669,044 B2 | 3/2014 | Chiu et al. | |
| 8,679,751 B2 | 3/2014 | Huang | |
| 8,721,642 B1 | 5/2014 | Sullivan | |
| 8,905,968 B2 | 12/2014 | Thomas | |
| 9,205,184 B2 | 12/2015 | Eckermann | |
| 9,211,163 B1 | 12/2015 | Jaramaz et al. | |
| 9,387,311 B1 | 7/2016 | Heilman et al. | |
| 9,770,180 B2 | 9/2017 | Radojicic | |
| 9,895,518 B2 | 2/2018 | Lad et al. | |
| 10,272,188 B1 | 4/2019 | Geiger et al. | |
| 10,695,545 B2 | 6/2020 | Hedstrom et al. | |
| 2002/0077682 A1 | 6/2002 | Lee et al. | |
| 2002/0123714 A1 | 9/2002 | Saul et al. | |
| 2002/0156482 A1 | 10/2002 | Scribner et al. | |
| 2002/0193285 A1 | 12/2002 | Hesson et al. | |
| 2002/0198579 A1 | 12/2002 | Khanna | |
| 2003/0004495 A1 | 1/2003 | Saul | |
| 2003/0014016 A1 | 1/2003 | Purdy | |
| 2003/0028137 A1 | 2/2003 | Levin | |
| 2003/0032915 A1 | 2/2003 | Saul | |
| 2003/0063509 A1 | 4/2003 | Yamasaki | |
| 2003/0072761 A1 | 4/2003 | LeBowitz | |
| 2003/0083698 A1 | 5/2003 | Whitehurst et al. | |
| 2003/0097082 A1 | 5/2003 | Purdy et al. | |
| 2003/0129134 A1 | 7/2003 | Chenard et al. | |
| 2003/0130577 A1 | 7/2003 | Purdy et al. | |

(56) References Cited

U.S. PATENT DOCUMENTS

| | | |
|---|---|---|
| 2003/0130651 A1 | 7/2003 | Lennox |
| 2003/0135196 A1 | 7/2003 | Hesson et al. |
| 2003/0163181 A1 | 8/2003 | Frazer et al. |
| 2003/0199802 A1 | 10/2003 | Barbut |
| 2004/0015133 A1 | 1/2004 | Karim |
| 2004/0030279 A1 | 2/2004 | Rubenstein et al. |
| 2004/0068221 A1 | 4/2004 | Silverberg et al. |
| 2004/0138125 A1 | 7/2004 | Wang |
| 2004/0138728 A1 | 7/2004 | Wong et al. |
| 2004/0142906 A1 | 7/2004 | Wang |
| 2004/0147987 A1 | 7/2004 | Ginsburg et al. |
| 2004/0210231 A1 | 10/2004 | Boucher et al. |
| 2004/0215162 A1 | 10/2004 | Putz |
| 2004/0220545 A1 | 11/2004 | Heruth et al. |
| 2005/0004504 A1 | 1/2005 | Frye et al. |
| 2005/0060006 A1 | 3/2005 | Pflueger et al. |
| 2005/0090801 A1 | 4/2005 | Racz et al. |
| 2006/0015160 A1 | 1/2006 | Larnard |
| 2006/0016751 A1 | 1/2006 | Ali et al. |
| 2006/0030027 A1 | 2/2006 | Ellson et al. |
| 2006/0045796 A1 | 3/2006 | Anderle et al. |
| 2006/0058836 A1 | 3/2006 | Bose et al. |
| 2006/0142783 A1 | 6/2006 | Lewis et al. |
| 2006/0175543 A1 | 8/2006 | Elefteriades |
| 2006/0184098 A1 | 8/2006 | Barmitz et al. |
| 2006/0224101 A1 | 10/2006 | Glenn |
| 2006/0254984 A1 | 11/2006 | Polyakov |
| 2006/0282043 A1 | 12/2006 | Pyles |
| 2007/0050002 A1 | 3/2007 | Elefteriades |
| 2007/0246406 A1 | 10/2007 | Dibel et al. |
| 2008/0045883 A1 | 2/2008 | Radojicic |
| 2008/0154181 A1 | 6/2008 | Khanna |
| 2008/0171990 A1 | 7/2008 | Zauner |
| 2008/0190848 A1 | 8/2008 | Oklejas |
| 2008/0249458 A1 | 10/2008 | Yamasaki |
| 2008/0249501 A1 | 10/2008 | Yamasaki |
| 2008/0319376 A1 | 12/2008 | Wilcox et al. |
| 2009/0076357 A1 | 3/2009 | Purdy |
| 2009/0082800 A1 | 3/2009 | Janardhan |
| 2009/0105737 A1 | 4/2009 | Fulkerson et al. |
| 2009/0171369 A1 | 7/2009 | Gayzik |
| 2009/0277850 A1 | 11/2009 | Adams et al. |
| 2010/0030196 A1 | 2/2010 | Hildebrand et al. |
| 2010/0145267 A1 | 6/2010 | Bishop et al. |
| 2010/0168665 A1 | 7/2010 | Skerven |
| 2010/0179509 A1 | 7/2010 | Pyles |
| 2010/0198195 A1 | 8/2010 | Nishtala et al. |
| 2010/0204672 A1 | 8/2010 | Lockhart et al. |
| 2010/0260815 A1 | 10/2010 | Kyle et al. |
| 2010/0280438 A1 | 11/2010 | Thomas |
| 2010/0305492 A1 | 12/2010 | Lad et al. |
| 2010/0324397 A1 | 12/2010 | Purdy |
| 2011/0029050 A1 | 2/2011 | Elefteriades et al. |
| 2011/0046547 A1 | 2/2011 | Mantle |
| 2011/0098623 A1 | 4/2011 | Zhang et al. |
| 2011/0190831 A1 | 8/2011 | Mafi et al. |
| 2011/0319824 A1 | 12/2011 | Pyles |
| 2012/0004625 A1 | 1/2012 | Velez-Rivera |
| 2012/0149021 A1 | 6/2012 | Yung et al. |
| 2012/0165757 A1 | 6/2012 | Purdy |
| 2012/0203142 A1 | 8/2012 | Bedell |
| 2012/0203290 A1 | 8/2012 | Warren et al. |
| 2012/0209367 A1 | 8/2012 | Prindle et al. |
| 2012/0232458 A1 | 9/2012 | Herschman |
| 2012/0234694 A1 | 9/2012 | Vecitis et al. |
| 2012/0253266 A1 | 10/2012 | Qureshi et al. |
| 2012/0302938 A1 | 11/2012 | Browd et al. |
| 2012/0330196 A1 | 12/2012 | Nita |
| 2013/0023814 A1 | 1/2013 | Bertrand et al. |
| 2013/0030411 A1 | 1/2013 | Kreck et al. |
| 2013/0035628 A1 | 2/2013 | Garrison et al. |
| 2013/0066331 A1 | 3/2013 | Chitre et al. |
| 2013/0085413 A1 | 4/2013 | Tsamir et al. |
| 2013/0131811 A1 | 5/2013 | Barreiro et al. |
| 2013/0158470 A1 | 6/2013 | Panotopoulos |
| 2013/0158564 A1 | 6/2013 | Harris et al. |
| 2013/0165903 A1 | 6/2013 | Webler et al. |
| 2013/0197422 A1 | 8/2013 | Browd et al. |
| 2013/0248450 A1 | 9/2013 | Kenley et al. |
| 2014/0066830 A1 | 3/2014 | Lad et al. |
| 2014/0166555 A1 | 6/2014 | Dibel et al. |
| 2014/0194840 A1 | 7/2014 | Eckermann |
| 2014/0276334 A1 | 9/2014 | Eckermann |
| 2014/0276660 A1 | 9/2014 | Eckermann |
| 2014/0299546 A1 | 10/2014 | Eckert et al. |
| 2014/0316373 A1 | 10/2014 | Dhall |
| 2014/0323857 A1 | 10/2014 | Mourad et al. |
| 2014/0358183 A1 | 12/2014 | Saunders et al. |
| 2015/0094644 A1 | 4/2015 | Lenihan et al. |
| 2015/0196742 A1 | 7/2015 | Browd et al. |
| 2015/0223832 A1 | 8/2015 | Swaney et al. |
| 2015/0224284 A1 | 8/2015 | Panotopoulos et al. |
| 2015/0238682 A1 | 8/2015 | Teranuma et al. |
| 2015/0238685 A1 | 8/2015 | Elias et al. |
| 2015/0257774 A1 | 9/2015 | Galdonik et al. |
| 2015/0328295 A1 | 11/2015 | Lodge et al. |
| 2016/0051801 A1 | 2/2016 | Vase |
| 2016/0101270 A1 | 4/2016 | Browd et al. |
| 2016/0136398 A1 | 5/2016 | Heilman et al. |
| 2016/0174995 A1 | 6/2016 | Turjman et al. |
| 2016/0303355 A1 | 10/2016 | Heilman et al. |
| 2016/0303356 A1 | 10/2016 | Heilman et al. |
| 2017/0000361 A1 | 1/2017 | Meyering et al. |
| 2017/0035950 A1 | 2/2017 | Meyering et al. |
| 2017/0035998 A1 | 2/2017 | Meyering et al. |
| 2017/0095649 A1 | 4/2017 | Vase et al. |
| 2017/0157374 A1 | 6/2017 | Hedstrom et al. |

FOREIGN PATENT DOCUMENTS

| | | |
|---|---|---|
| CA | 2793672 A1 | 9/2011 |
| CA | 2936349 A1 | 7/2015 |
| CN | 101288783 A | 10/2008 |
| CN | 101653637 A | 2/2010 |
| CN | 202409608 U | 9/2012 |
| CN | 102973305 A | 3/2013 |
| CN | 203816046 U | 9/2014 |
| CN | 203935243 U | 11/2014 |
| CN | 105361923 A | 3/2016 |
| EP | 515007 B1 | 12/1996 |
| EP | 1331019 A2 | 7/2003 |
| EP | 2217315 B1 | 5/2012 |
| EP | 2583744 A1 | 4/2013 |
| EP | 2695633 A1 | 2/2014 |
| EP | 2882483 A1 | 12/2014 |
| GB | 2365344 A | 2/2002 |
| JP | H03504681 A | 10/1989 |
| JP | 2001509712 A | 7/2001 |
| JP | 2001513349 A | 9/2001 |
| JP | 2002514096 A | 5/2002 |
| JP | 2003515394 A | 5/2003 |
| JP | 2003250881 A | 9/2003 |
| JP | 2003526398 A | 9/2003 |
| JP | 2004508109 A | 3/2004 |
| JP | 2004236792 A | 8/2004 |
| JP | 2004528062 A | 9/2004 |
| JP | 2006514857 A | 5/2006 |
| JP | 2006525827 A | 11/2006 |
| JP | 2010505556 A | 2/2010 |
| JP | 2010520446 A | 6/2010 |
| JP | 2011526799 A | 10/2011 |
| JP | 2012066103 A | 4/2012 |
| RU | 2100965 C1 | 1/1998 |
| RU | 2158613 C2 | 11/2000 |
| RU | 2290974 C1 | 1/2007 |
| RU | 2312678 C1 | 12/2007 |
| RU | 2314838 C2 | 1/2008 |
| WO | 8909629 A1 | 10/1989 |
| WO | 9205864 A1 | 4/1992 |
| WO | 9802202 A1 | 1/1998 |
| WO | 9833535 A1 | 8/1998 |
| WO | 9907276 A1 | 2/1999 |
| WO | 0041762 A1 | 7/2000 |
| WO | 0043056 A1 | 7/2000 |

(56)                    References Cited

FOREIGN PATENT DOCUMENTS

| WO | 0051669 | A1 | 9/2000 |
|---|---|---|---|
| WO | 0139819 | A2 | 6/2001 |
| WO | 0154766 | A1 | 8/2001 |
| WO | 0211703 | A1 | 2/2002 |
| WO | 0220083 | A2 | 3/2002 |
| WO | 0232494 | A2 | 4/2002 |
| WO | 02056937 | A2 | 7/2002 |
| WO | 03015710 | A2 | 2/2003 |
| WO | 03020208 | A2 | 3/2003 |
| WO | 03057306 | A1 | 7/2003 |
| WO | 2004041314 | A1 | 5/2004 |
| WO | 2004060463 | A1 | 7/2004 |
| WO | 2004072647 | A1 | 8/2004 |
| WO | 2004093945 | A1 | 11/2004 |
| WO | 2004105839 | A1 | 12/2004 |
| WO | 2005035025 | A1 | 4/2005 |
| WO | 2005044335 | A2 | 5/2005 |
| WO | 2005044847 | A1 | 5/2005 |
| WO | 2006017763 | A2 | 2/2006 |
| WO | 2006079007 | A2 | 7/2006 |
| WO | 2006086195 | A2 | 8/2006 |
| WO | 2007013945 | A2 | 2/2007 |
| WO | 2007110643 | A1 | 10/2007 |
| WO | 2008105959 | A2 | 9/2008 |
| WO | 2008107652 | A1 | 9/2008 |
| WO | 2009114046 | A2 | 9/2009 |
| WO | 2009140202 | A1 | 11/2009 |
| WO | 2009155384 | A1 | 12/2009 |
| WO | 2009155614 | A2 | 12/2009 |
| WO | 2010014447 | A2 | 2/2010 |
| WO | 2010123558 | A1 | 10/2010 |
| WO | 2010127071 | A1 | 11/2010 |
| WO | 2011060317 | A2 | 5/2011 |
| WO | 2011114260 | A1 | 9/2011 |
| WO | 2011150323 | A2 | 12/2011 |
| WO | 2012099984 | A1 | 7/2012 |
| WO | 2013034602 | A1 | 3/2013 |
| WO | 2013052951 | A2 | 4/2013 |
| WO | 2014023551 | A1 | 2/2014 |
| WO | 2014023552 | A1 | 2/2014 |
| WO | 2014039780 | A1 | 3/2014 |
| WO | 2014160481 | A1 | 8/2014 |
| WO | 2015104631 | A1 | 7/2015 |
| WO | 2015109260 | A1 | 7/2015 |
| WO | 2015157320 | A1 | 10/2015 |
| WO | 2016007553 | A1 | 1/2016 |

OTHER PUBLICATIONS

Japanese Rejection of Appeal for related Japanese patent application No. 2009-531646, mailed Jan. 25, 2016 (13 pages).

European Search Report and Opinion for European Patent Application No. 07873762.4, dated May 27, 2011 (11 pages).

International Search Report and Written Opinion of the International Searching Authority for International Patent Application for International Patent Application No. PCT/US2016/036626, mailed Sep. 8, 2016.

International Search Report and Written Opinion of the International Searching Authority for International Patent Application No. PCT/US2010/01186, mailed Jun. 21, 2010 (7 pages).

International Search Report and Written Opinion of the International Searching Authority for International Patent Application No. PCT/US2007/80834, mailed Oct. 28, 2008 (8 pages).

Arnold et al; Electro-Rotation: Develpoment of a Technique for Dielectric Measurements on Individual Cells and Particles, Journal of Electrostatics, vol. 21, pp. 151-191, 1988.

Arvin et al; "The Role of Inflammation and Cytokines in Brain Injury," Neuroscience and Biobehavorial Reviews, vol. 20, No. 3, pp. 445-452, 1996.

Banci et al; "Metal-free superoxide dismutase forms soluble oligomers under physiological conditions: A possible general mechanism for familial ALS," PNAS, vol. 104, No. 27, pp. 11263-11267, Jul. 3, 2007.

Bayer et al; "Evaluation of the safety and immunogenicity of synthetic AB42 (AN1792) in patients with AD," Neurology, vol. 64, pp. 94-101, Jan. 2005.

Becker et al; "Separation of Human Breast Cancer Cells from Blood by Differential Dielectric Affinity," Proc. Natl. Acad. Sci, vol. 92, pp. 860-864, Jan. 1995.

Becker et al; "The Removal of Human Leukemia Cells for Blood Using Interdigitated Microelectrodes," J. Phys.D: Appl. Phys; vol. 27, pp. 2659-2662, 1994.

Blennow et al; "Alzheimer's disease," Lancet, vol. 368, pp. 387-403, Jul. 29, 2006.

Buzzigoli et al; "Plasmapherisis treatment in Guillain-Barre syndrome: potential benefit over intravenous Immunoglobin," Anaesth Intensive Care, vol. 38, No. 2, pp. 387-389, Mar. 2010.

Cambria et al; "Clinical Experience with Epidural Cooling for Spinal Cord Protection during Thoracic and Thoracoabdominal Aneurysm Repair," Journal of Vascular Surgery, vol. 25, No. 2, pp. 234-243, Feb. 1997.

Caughey et al; "Protofibrils, pores, fibrils, and neurodegeneration: separating the responsible protein aggregates from the innocent bystanders," Annu. Rev. Neurosci; vol. 26, pp. 267-298, 2003.

Cook, "Combined Spinal-Epidural Techniques," Anaesthesia, vol. 55, pp. 42-64, 2000.

Covaciu et al; "Brain Temperature in Volunteers Subjected to Intranasal Cooling," Intensive Care Med; vol. 37, No. 8,Abstract (1 page), Aug. 2011.

Dawson et al; "Molecular Pathways of Neurodegeneration in Parkinson's Disease," Science, vol. 32, pp. 819-822, Oct. 21, 2003.

Dekosky et al; "Looking Backward to Move Forward: Early Detection of Neurodegenerative Disorders," vol. 302, pp. 830-834, Oct. 31, 2003.

Delhaas, "Extradural and Subarachnoid Catheterization Using the Seldinger Technique," British Journal of Anaesthesia, vol. 76, pp. 149-150, 1996.

Dias-Santagata et al; "Oxidative stress mediates tau-induced neurodegeneration in *Drosophila*," Journal of Clinical Investigation, vol. 117, pp. 236-245, Jan. 2007.

Dunnett et al; Prospects for new restorative and neuroprotective treatments in Parkinson's disease, Nature, vol. 399, pp. A32-A38, Supp, Jun. 24, 1999.

Elefteriades, et al; "Litigation in Nontraumatic Aortic Diseases—A Tempest in the Malpractice Maelstrom," Cardiology vol. 109, pp. 263-272, 2008.

Enchev et al; "Historical Trends of Neuroendoscopic Surgical Techniques in the Treatment of Hydrocephalus," Neurosurgery Review, vol. 31, pp. 249-262, 2008.

Gascoyne et al; Dielectrophoretic Separation of Cancer Cells from Blood IEEE Transactions of Industry Applications, vol. 33, No. 3, pp. 670-678, May/Jun. 1997.

Gascoyne et al; "Isolation of Rare Cells from Cell Mixtures by Dielectrophoresis," Electrophoresis, vol. 30, No. 8, pp. 1388-1398, Apr. 2009.

Gascoyne et al.; "Particle Separation by Dielectrophoresis," Electrophoresis, vol. 23, No. 13, pp. 1973-1983, Jul. 2002.

Gilman et al; "Clinical effects of AB immunization (AN1792) in patients with AD in an interrupted trial," Neurology, pp. 1553-1562, vol. 64, May 2005.

Glabe, "Common mechanisms of amyloid oligomer pathogenisis in degenerative disease," Neurobiology of Aging, pp. 570-575, vol. 27, 2006.

Haltiwanger, "The Electrical Properties of Cancer Cells," www.royalrife.com/haltiwanger1 (62 pages), Jul. 2010.

Han et al; "An Electrorotation Technique for Measuring the Dielectric Properties of Cells with Simultaneous Use of Negative Quadropolar Dielectrophoresis and Electrorotation," The Royal Society of Chemistry, Analyst, pp. 1529-1537, vol. 138, Mar. 2006.

Hansson et al; Association between CDF biomarkers and incipient Alzheimer's disease in patients with mild cognitive impairment: a follow-up study, Lancet Neurol; pp. 228-234, vol. 5, Mar. 2006.

Helmy et al; "The Cytokine Response to Human Traumatic Brain Injury: Temporal Profiles for Cerebral Parenchymal Production," Journal of Cerebral Blood Flow & Metabolism, pp. 658-670, vol. 31, 2011.

(56) References Cited

OTHER PUBLICATIONS

Hock et al; Antibodies against beta-amyloid slow cognitive decline in Alzheimer's disease, pp. 547-554, vol. 38, May 22, 2003.

Hohfeld, et al; "Autoimmune concepts of multiple sclerosis as a basis for selective immunotherapy: From pipe dreams to (therapeutic) piplelines," PNAS, pp. 14599-14606, vol. 101, Suppl. 2, Oct. 5, 2004.

Huang et al; Electrode Design for Negative Dielectrophoresis, Measurement Science and Technology, pp. 1142-1146, vol. 2, Dec. 1991.

Janus et al; "A beta peptide immunization reduces behavorial impairment and plaques in a model of Alzheimer's disease in a model of Alzheimer's disease," Nature, pp. 979-982, vol. 408, Dec. 2000.

Jones et al; "Multipolar Dielectrophoretic and Electrorotation Theory," Journal of Electrostatics, pp. 121-134, vol. 37, 1996.

Kessler et al; "Endothelin-1 levels in plasma and cerebrospinal fluid of patients with cerebral vasospasm after aneurysmal subarachnoid hemorrhage," Surgical Neurology, pp. S1:2-S1:5, vol. 64, 2005.

Koo et al; "Amyloid diseases: Abnormal protein aggregation in neurodegeneration," Proc. Natl. Acad. Sci; pp. 9989-9990, vol. 96, Aug. 1999.

Kuwabara et al; "Intravenous immunoglobulin therapy for Guillain-Barre syndrome with IgG anti-GM1 antibody," Miscle & Nerve, Jan. 2001, pp. 53-58, Jan. 2001.

Lau et al; "Tau Protein Phosphorylation as a Therapeutic Target in Alzheimer's Disease," Current Topics in Medicinal Chemistry, pp. 395-415, vol. 2, 2002.

Levi et al; "Clinical Application of Modest Hypothermia After Spinal Cord Injury," J. Neurotrauma, pp. 407-415, vol. 26, No. 3, Abstract (1 page), Mar. 2009.

Li et al; "Continuous Dielectrophoretic Cell Separation Microfluidic Device," The Royal Society of Chemistry, Lab Chip, pp. 239-248, vol. 7, 2007.

"LiquoGuard", Moller Medical, Brochure, 2 pages, published on or before 2015.

MacDonald et al; "Cerebral vasospasm after subarachnoid hemorrhage: the emerging revolution," Nature Clinical Practice, Neurology, pp. 256-263, vol. 3, No. 5, May 2007.

Madeira-Lopes et al; Comparative Study of the Temperature Profiles of Growth and Death of the Pathogenic Yeast Cryptococcus Neoformans and the non-pathogenic Cryptococcus Albidus, Journal of Basic Microbiology, pp. 43-47, vol. 26, 1986.

Markx et al; "Dielectrophoretic Separation of Bacteria Using a Conductivity Gradient," Journal of Biotechnology, pp. 175-180, vol. 51, Dec. 1996.

Markx et al.; "Dielectrophoretic Separation of Cells: Continuous Separation," Biotechnology and Bioengineering, pp. 337-343, vol. 45, No. 4, Feb. 1995.

Marszalek et al; "Determination of Electric Parameters of Cell Membranes by a Dielectrophoresis Method," Biophysical Journal, vol. 59, pp. 982-987, May 1991.

Mascia et al; "Temporal Relationship Between Endothelin-1 Concentrations and Cerebral Vasospasm in Patients with Aneurysmal Subarachnoid Hemorrhage—Editorial Comment: Endothelin-1 in Vasospasm After SAH," Stroke, pp. 1185-1190, May 2001.

McCulloch et al; "A radical approach to stroke therapy," PNAS, vol. 98, No. 20, pp. 10989-10991, Sep. 25, 2001.

McKeating et al; "Cytokines and Adhesion in Acute Brain Injury," British Journal of Anaesthesia, vol. 80, pp. 77-84, 1998.

McKhann et al; "Plasmapherisis and Guillan-Barre syndrome: analysis of prognostic factors and the effect of plasmapheresis," Annals of Neurology, vol. 23, pp. 347-353, No. 4, Apr. 1988.

Melnikova, "Therapies for Alzheimer's disease", Nature Reviews, vol. 6, pp. 341-342, May 2007.

Misaki et al; "Contrast-Enhanced Fluid-Attenuated Inversion Recovery MRI is Useful to Detect the CSF Dissemination of Glioblastoma," Journal of Computer Assisted Tomography, vol. 25, No. 6, pp. 953-956, 2001.

Monsonego et al; "Immunotherapeutic Approaches to Alzheimer's Disease," Science, vol. 302, pp. 834-838, Oct. 31, 2003.

Morgan et al; "A beta peptide vaccination prevents memory loss in an animal model of Alzheimer's disease," Nature, vol. 408, pp. 982-985, Dec. 2000.

Morganti-Kossman et al; "Production of Cytokines Following Brain Injury : Beneficial and Deleterious for the Damaged Tissue," Molecular Psychiatry, vol. 2, pp. 133-136, 1997.

Nicoll et al; "Abeta species removal after abeta42 immunization," Journal of Neuropathology Exp. Neurol; vol. 65, No. 11, pp. 1040-1048, Nov. 2006.

Noseworthy, "Progress in determining the causes and treatment of multiple sclerosis," vol. 399, pp. A40-A47, Supp. Jun. 24, 1999.

Onda et al; "Cerebral Glioblastoma with Cerebrospinal Fluid Dissemination: A Clinicopathological Study of 14 Cases Examined by Complete Autopsy," Neurosurgery, vol. 25, No. 4 pp. 1040-1048, 1989.

Orgogozo et al; "Subacute meningoencephalitis in a subset of patients with AD after AB immunization," Neurology, vol. 61, pp. 46-54, Jul. 2003.

Park, et al., "3-D Electrode Designs for Flow-through Dielectrophoretic Systems", Electrophoresis, 26(19): 3745-3757, Oct. 2005.

Parkhill et al; "The genome sequence of the food-borne pathogen Campylobacter jejuni reveals hypervariable sequences," Nature, vol. 403, pp. 665-668, Feb. 10, 2000.

Perfect, "Cryptococcous Neoformans: The Yeast that Likes it Hot," FEMS Yeast Res; vol. 6, pp. 463-468, 2006.

Pethig et al; "Applicants of Dielectrophoresis in Biotechnology," Tibtech, vol. 15, pp. 426-432, Oct. 1997.

Pethig, "Dielectrophoresis: Status of the Theory, Technology and Applications," Biomicrofluidics, vol. 4, pp. 022811-1-35, 2010.

Pethig, "Dielectrophoresis: Using Inhomogeneous AC Electrical Fields to Separate and Manipulate Cells," Critical Reviews in Biotechnology, vol. 16, No. 4, pp. 331-348, 1996.

Polderman et al; "Therapeutic Hypothermia and Controlled Normothermia in the Intensive Care Unit: Practical Considerations, Side Effects, and Cooling Methods," Crit. Care Med; vol. 37, No. 3 Abstract (1 page), pp. 1101-1120, Mar. 2009.

Reiber, "Proteins in cerebrospinal fluid and blood: Barriers, CSF flow rate and source-related dynamics", Reiber Restorative Neurology and Neuroscience, vol. 21, pp. 79-96, 2003.

Roberson et al; "100 Years and Counting: Prospects for Defeating Alzheimer's Disease," Science, vol. 314, pp. 781-784, Nov. 3, 2006.

Rowland, "Amyotrophic Lateral Sclerosis: Human Challenge for Neuroscience," Proc. Natl. Acad. Sci; vol. 92, pp. 1251-1253, Feb. 1995.

Shoulson, "Experimental Therapeutics of Neurodegenerative Disorders: Unmet Needs," Science, vol. 282, pp. 1072-1074, Nov. 6, 1998.

Steece-Collier et al; "Etiology of Parkinson's disease: Genetics and environment revisited," PNAS, vol. 99, No. 22, pp. 13972-13974, Oct. 29, 2002.

Tay et al; "Electrical and Thermal Characterization of a Dielectrophoretic chip with 3D Electrodes for Cells Manipulation," Electrochimica. Acta; vol. 52, pp. 2862-2868, 2007.

Taylor et al; "Toxic Proteins in Neurodegenerative Disease", Science, vol. 296, pp. 1991-1995, Jun. 14, 2002.

"External CSF Drainage," Aqueduct Neurosciences, 2 pages, Jul. 2014.

"Therapeutic Hypothermia for Spinal Cord Injury," Crit. Care Med. Vol. 37, Supp. 7, Abstract (1 page) pp. S238-S242, Jul. 2009.

World Journal of Radiology, Journal of Radiology, vol. 4. No. 6, pp. 241-290, Jun. 28, 2012.

Valentine, et al; "Misfolded CuZnSOD and amyotrophic lateral sclerosis," PNAS, vol. 100, No. 7, pp. 3617-3622, Apr. 1, 2003.

Vernino et al; "Autoimmune encephalopathies," The Neurologist, vol. 13, No. 3, pp. 140-147, May 2007.

Voldman, "Electrical Forces for Microscale Cell Manipulation," Annu. Rev. Biomed. Eng. vol. 8, pp. 425-454, 2006.

Weis et al; "Noninvasive Monitoring of Brain Temperature During Mild Hypothermia," Magn. Reson. Imaging, vol. 27, No. 7, Abstract (1 page), pp. 923-932, Sep. 2009.

(56)                    References Cited

OTHER PUBLICATIONS

Wollinsky et al; "CSF filtration is an effective treatment of Guillain-Barre syndrome: A randomized clinical trial," Neurology, vol. 57, pp. 774-780, Sep. 2001.

Yuki et al; "Carbohydrate mimicry between human ganglioside GM1 and Campylobacter Jejuni lipooligosaccharide causes Guillain-Barre syndrome," PNAS, vol. 101, No. 31, pp. 11404-11409, Aug. 3, 2004.

Ziebell et al; "Involvement of Pro- and Anti-Inflammatory Cytokines and Chemokines in the Pathophysiology of Traumatic Brain Injury," Neurotherapeutics: The Journal of the American Society for Experimental Neurotherapeutics, vol. 7, pp. 22-30, Jan. 2010.

European Office Action for European Patent No. 07873762.4 , dated Dec. 7, 2016 (5 pages).

Mahon et al; "North American Clinical Experience with the EKOS MicroLysUS Infusion Catheter for the Treatment of Embolic Stroke," AJNR Am j. Neuroradiology, vol. 24, pp. 534-538.

Rogers et al; "Precutaneous aspiration of brain tumor cysts via the Ommaya reservoir system," Neurology, vol. 41, pp. 279-282.

Siddiqui et al; "Use of the Penumbra System 054 plus Low Dose Thrombolytic Infusion for Mulitfocal Venous Sinus Thrombosis," Interventional Neuroradiology, vol. 18, pp. 314-319, 2012.

Spielberg, GmbH & Co. KG, "EVD—Catheters," downloaded on Nov. 3, 2016 from website. http://www.spielberg.de/products/drainage/silverline_evd_catheter_3001002.html (1 page).

Wagner et al; "Ultra-early clot aspiration after lysis with tissue plasminogen activator in a porcine model of Intracerebral hemmorgage: edema reduction and blood-brain barrier protection," J. Neurosurg; vol. 90, pp. 491-498, Mar. 1999.

Ziu et al; "A Series of Cerebral Venous Sinus Thromboses Treated with Intra-Arterial tPA infused over Ten Hours with a 0.027-inch Catheter and Literature Review," pp. 1-13, Jun. 23, 2016.

International Search Report for International Patent Application No. PCT/US2016/064721, mailed Feb. 17, 2017 (3 pages).

International Search Report for International Patent Application No. PCT/US2016/055724, mailed Feb. 15, 2017 (7 pages).

Written Opinion of the International Searching Authority for International Patent Application No. PCT/US2016/064721, mailed Feb. 17, 2017 (7 pages).

Written Opinion of the International Searching Authority for International Patent Application No. PCT/US2016/055724, mailed Feb. 15, 2017 (11 pages).

Firer, "Efficient elution of functional proteins in affinity chromatography," J. Biochem. Biophys. Methods 49, pp. 433-442, 2001.

Extended EP Search Report dated Mar. 4, 2019 for EP application No. 16833454.8, 7 pages.

Madeira-Lopes, et al., "Comparative study of the temperature profiles of growth and death of the pathogenic yeast Cryptococcus neoformans and the non-pathogenic Cryptococcus albidus", J. Basic Microbiol., 26: 43-47, 1986.

Dias, et al., "The hydrophobic effect and its role in cold denaturation", Cryobiology, 60: 91-99, 2010.

Chevrefils, et al., "UV Dose Required to Achieve Incremental Log Inactivation of Bacteria, Protozoa and Viruses", IUVA News, 8(1): 38-45, Mar. 2006.

Prates, et al., "Photodynamic therapy can kill Cryptococcus neoformans in in vitro and in vivo models", Proc. of SPIE, vol. 7165, 2009.

Pitera, et al., "Dielectric Properties of Proteins from Simulation: The Effects of Solvent, Ligands, pH, and Temperature", Biophysical Journal, 80(6): 2546-2555, Jun. 2001.

Han, et al., "Lateral-Driven Continuous Dielectrophoretic Microseparators for Blood Cells Suspended in a Highly Conductive Medium", Lab on a Chip, 8(7):1079-1086, Jun. 27, 2008.

Baumann, et al., "The Electrical Conductivity of Human Cerebrospinal Fluid at Body Temperature", IEEE Transactions on Biomedical Engineering, 44(3): 220-223, Mar. 1997.

Huang, et al., "Electrode Design for Negative Dielectrophoresis", Measurement Science and Technology, P(12): 1142-1146, Dec. 1, 1991.

Chen, et al., "A 3D Paired Microelectrode Array for Accumulation and Separation of Microparticles", J. of Micromechanics and Microengineering, 16(7): 1162-1169, Apr. 28, 2006.

Stephens et al; "The Dielectrophoresis Enrichment of CD34 Cells from Peripheral Blood Stem Cell Harvests," Bone Marrow Transplantation, vol. 18, pp. 777-782, 1996.

* cited by examiner

More Cranial

More Caudal

FIG. 4

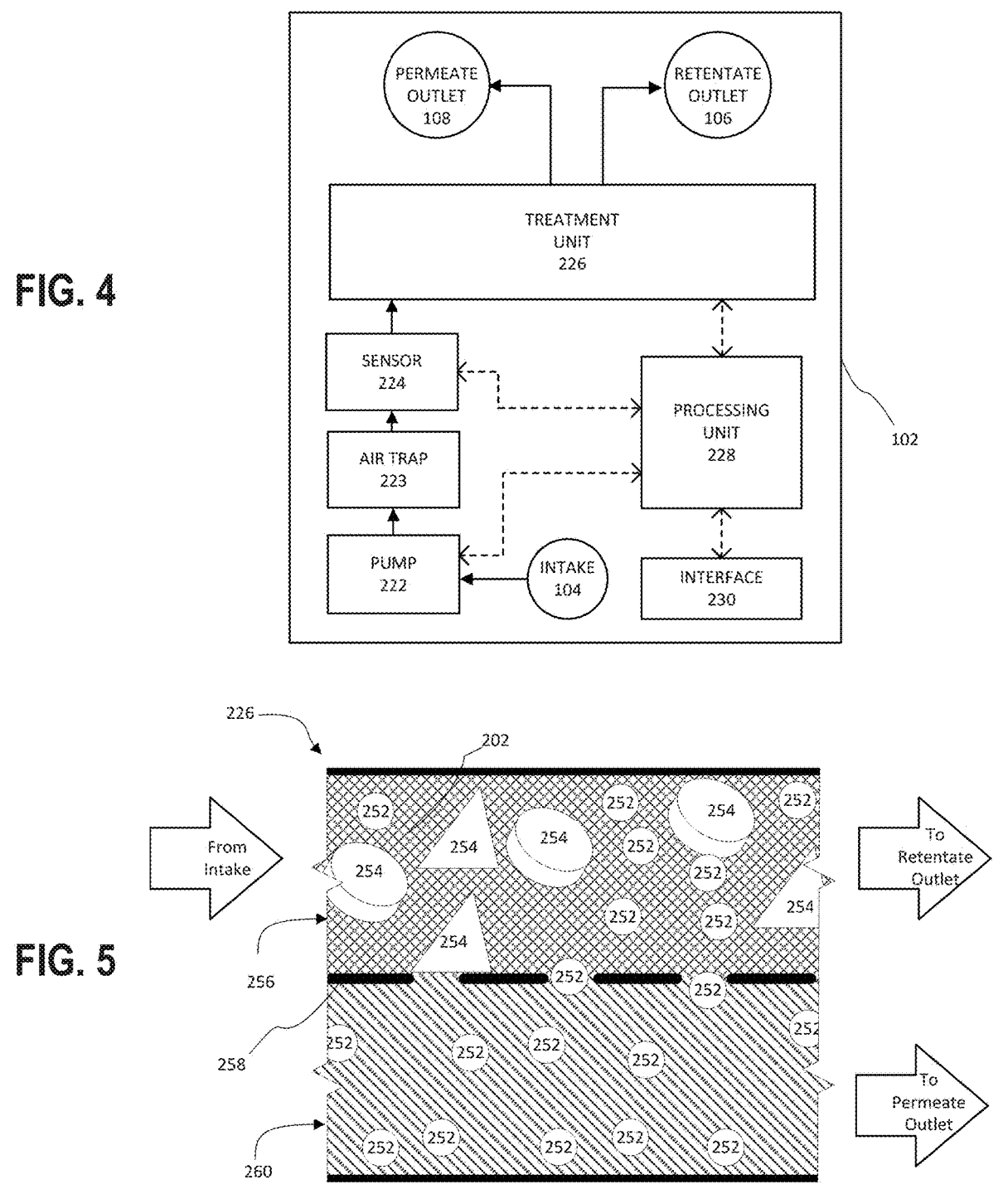

PERMEATE OUTLET 108

RETENTATE OUTLET 106

TREATMENT UNIT 226

SENSOR 224

AIR TRAP 223

PUMP 222

INTAKE 104

PROCESSING UNIT 228

INTERFACE 230

From Intake

To Retentate Outlet

To Permeate Outlet

252

254

256

258

260

600
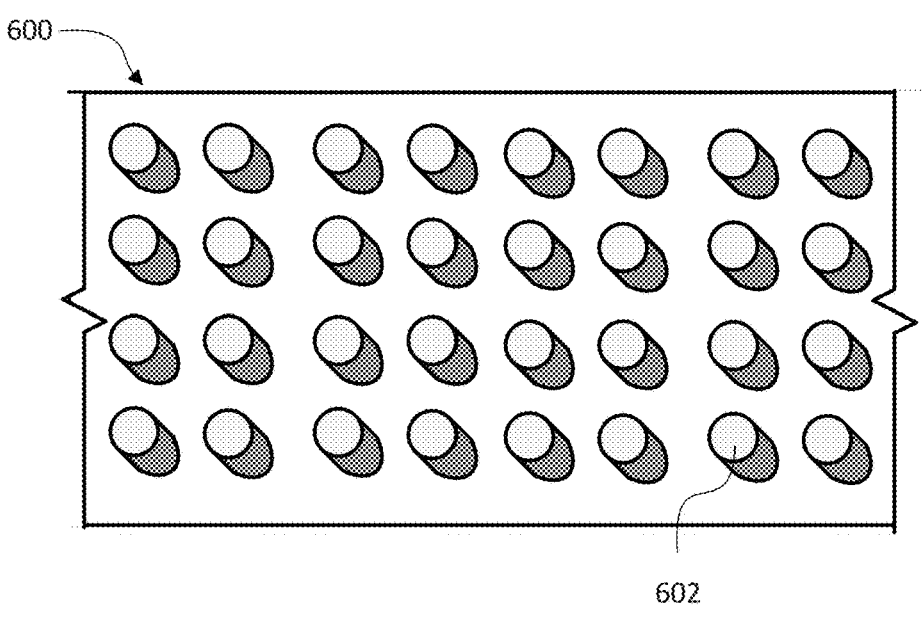
602
FIG. 13
600
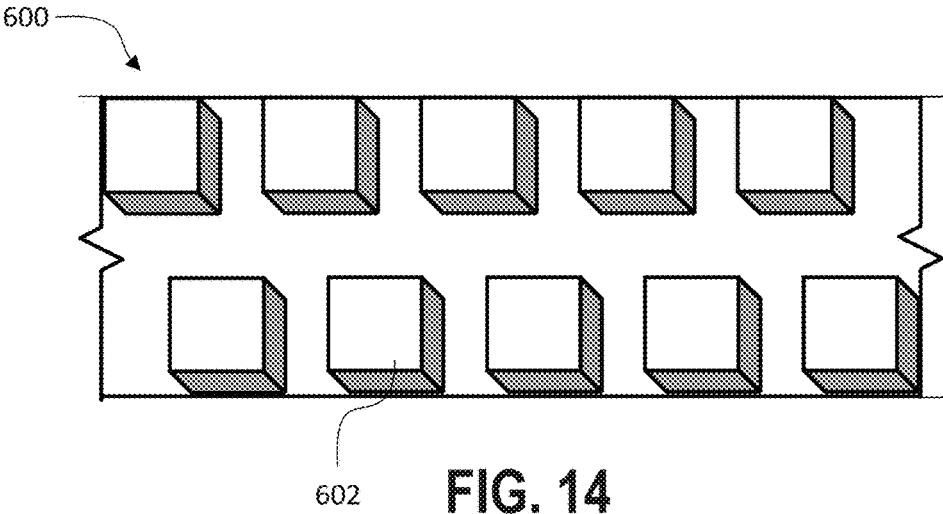
602          FIG. 14
600
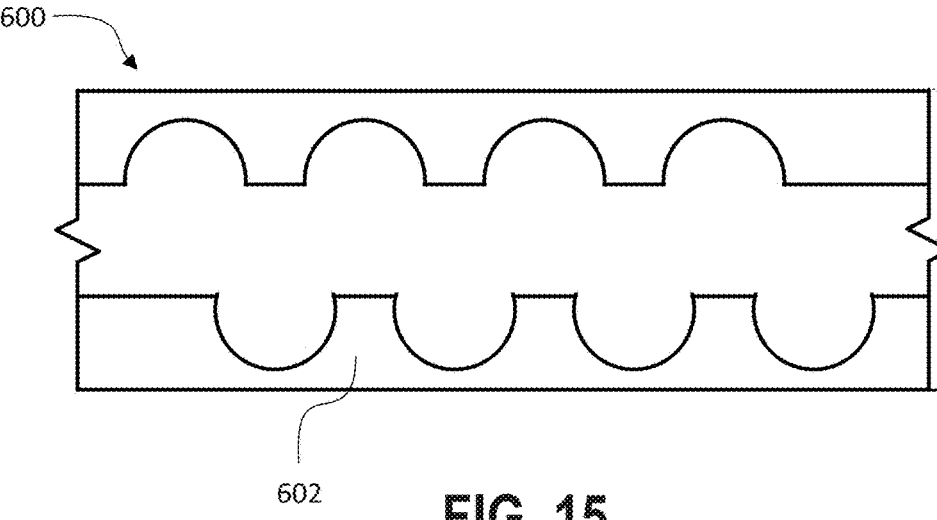
602          FIG. 15

SYSTEMS AND METHODS FOR THE CONDITIONING OF CEREBROSPINAL FLUID

CROSS-REFERENCE TO RELATED APPLICATIONS

This application is a continuation of U.S. patent application Ser. No. 16/742,870, filed Jan. 14, 2020, which issued as U.S. Pat. No. 11,577,060, which is a continuation of U.S. patent application Ser. No. 15/367,592, filed Dec. 2, 2016, which issued as U.S. Pat. No. 10,695,545, which claims the benefit of priority under 35 U.S.C. § 119 of the earlier filing date of U.S. Provisional Patent Application No. 62/263,305, filed Dec. 4, 2015, entitled "Systems and Methods for the Conditioning of Cerebrospinal fluid," each of which is hereby fully incorporated by reference for any and all purposes as if fully set forth herein in their entireties.

Embodiments described in this application may be used in combination or conjunction with the subject matter described in one or more of the following, each of which is hereby fully incorporated by reference for any and all purposes as if set forth herein in their entireties:

U.S. Pat. No. 8,435,204, entitled "Cerebrospinal Fluid Purification System," which issued May 7, 2013, which is the U.S. National Phase entry of International Patent Application Number PCT/US2007/080834, filed Oct. 9, 2007, which claims the benefit of priority of U.S. Provisional Application No. 60/828,745, filed on Oct. 9, 2006;

U.S. patent application Ser. No. 14/743,652, filed Jun. 18, 2015, entitled "Devices and Systems for Access and Navigation of Cerebrospinal Fluid Space," which claims the benefit of priority of U.S. Provisional Application No. 62/038,998, filed on Aug. 19, 2014;

U.S. patent application Ser. No. 13/801,215, filed Mar. 13, 2013, entitled "Cerebrospinal Fluid Purification System," which is a continuation of U.S. patent application Ser. No. 12/444,581, filed Jul. 1, 2010, which issued as U.S. Pat. No. 8,435,204 and is the U.S. National Phase entry of International Patent Application Number PCT/US2007/080834, filed Oct. 9, 2007, which claims the benefit of priority of U.S. Provisional Application No. 60/828,745, filed on Oct. 9, 2006; and U.S. patent application Ser. No. 15/287,174, filed Oct. 6, 2016, entitled "Devices and Methods for Providing Focal Cooling to the Brain and Spinal Cord," which claims the benefit of priority of U.S. Provisional Patent Application No. 62/237,867, filed Oct. 6, 2015."

BACKGROUND

Cerebrospinal fluid (CSF) is a generally clear, colorless fluid that is produced in the ventricles, specifically the choroid plexuses, in the brain. The choroid plexus produces approximately 500 milliliters of CSF daily to accommodate flushing or recycling of CSF to remove toxins and metabolites, which happens several times per day. From the choroid plexus, CSF flows slowly through a channel (canal) into the spinal column, and then into the body. CSF is found in the space between the pia mater and the arachnoid mater, known as the subarachnoid space. CSF is also found in and around the ventricular system in the brain, which is continuous with the central canal of the spinal cord. It may be desirable to remove, condition, and return CSF to treat various medical conditions. The present disclosure sets forth treatment modalities, methodologies, and therapies in this context.

The information included in this Background section of the specification, including any references cited herein and any description or discussion thereof, is included for technical reference purposes only and is not to be regarded subject matter by which the scope of the invention is to be bound.

SUMMARY

In some embodiments, the performance of CSF-treatment systems may be improved by various treatments of CSF, including heating the CSF to a target temperature, cooling the CSF to a target temperature, increasing CSF flow rate, applying light treatment to the CSF, applying an osmotic gradient to lyse cells, separating cells via their dielectric properties, applying spiral and/or centrifugal separation, binding additives to target particles within the CSF, other treatment techniques, or combinations of these.

BRIEF DESCRIPTION OF THE DRAWINGS

FIG. 4 illustrates a block diagram of a treatment system, according to some embodiments, with solid arrows indicating an example fluid flow path and dashed arrows indicating an example flow path for signals or information.

FIG. 5 illustrates a filter portion of a treatment system, according to some embodiments.

FIG. 13 illustrates a dielectrophoresis system having 3D cylindrical electrodes according to some embodiments.

FIG. 14 illustrates a dielectrophoresis system having 3D castellated electrodes according to some embodiments.

FIG. 15 illustrates a dielectrophoresis system having a 3D semi-circle electrode design according to some embodiments.

DETAILED DESCRIPTION

Figure 1:
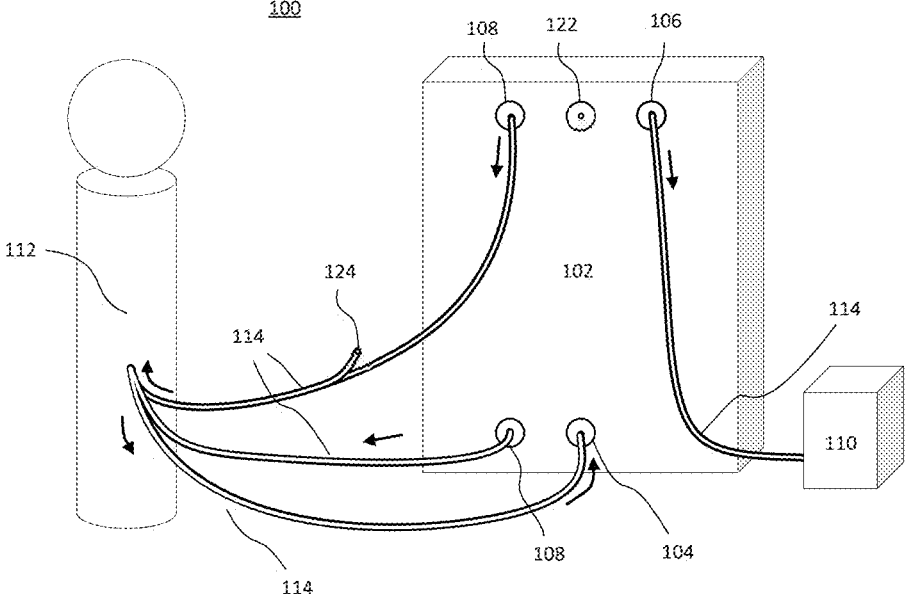
FIG. 1 illustrates a system for treating biologic fluids according to some embodiments, with solid arrows indicating an example fluid flow direction.

Disclosed embodiments generally relate to improved systems and methods for treating biologic fluids of a human or animal subject. In some embodiments, a filter, such as a tangential flow filter (TFF), may be used to separate cerebrospinal fluid (CSF) into permeate and retentate. The permeate may be returned to the subject. In some embodiments, the retentate may subjected to additional conditioning. For example, it may be filtered again, such as through one or more additional tangential flow filters or other methods of filtering. During operation of the system, various parameters may be modified, such as flow rate and pressure. Certain systems and methods described herein may be combined with other systems and methods for conditioning, removing, or otherwise processing biological materials, such as those discussed in U.S. Pat. No. 8,435,204. In some embodiments, treating the biologic fluids may include heating CSF to a target temperature, cooling CSF to a target temperature, applying light treatment to CSF, separating cells via their dielectric properties, applying spiral and/or centrifugal separation, introducing additives to the CSF, applying combinations thereof, or other techniques FIG. 1 illustrates a system 100 for the treatment of biologic fluids according to certain embodiments, including a treatment system 102, an intake 104, a retentate outlet 106, a permeate outlet 108, a vessel 110, a treatment site 112, and tubing 114. The arrows represent an example direction that fluid may take through the system.

In certain embodiments, the treatment system 102 is a device or combination of devices that is configured to filter, concentrate, dialyze, separate, or otherwise treat or condition the fluid, its contents, or both. In some embodiments, the treatment system 102 may treat the subject by modifying the fluid. For example, the treatment system 102 may treat a portion of the subject's spinal cord or brain by cooling the withdrawn fluid and returning the cooled fluid to cause local cooling. The treatment system 102 may include a tangential flow filtration system (for example, as shown and described in relation to FIG. 5) or other system configured to filter fluid. In some embodiments, the treatment system 102 receives the fluid through an intake 104 and returns the fluid through one or more outlets. For example, in certain embodiments, the treatment system 102 receives the fluid through the intake 104 and separates the fluid into retentate and permeate. The retentate exits the treatment system 102 through a retentate outlet 106, and the permeate exits the treatment system 102 through a permeate outlet 108.

The intake 104 may be a port through which fluid enters the treatment system 102. The retentate outlet 106 may be an outlet through which retentate exits the treatment system 102. The permeate outlet 108 may be an outlet through which permeate exists the treatment system 102.

The intake 104, retentate outlet 106, and permeate outlet 108 may be any kind of ports through which material or fluid may flow. These components may be configured to be in fluid connection by tubing 114. The components 104, 106, 108, 114 may include various fittings to facilitate the connection, including but not limited to compression fittings, flare fittings, bite fittings, quick connection fittings, Luer-type fittings, threaded fittings, and other components configured to enable fluid or other connection between two or more components. In addition to fittings, the components 104, 106, 108, 114 also may include various elements to facilitate use of the system 100, including but not limited to various valves, flow regulators, adapters, converters, stopcocks, reducers, and other elements.

In certain embodiments, there may be one or more outlets, such as one or more permeate outlets 108 and/or retentate outlets 106. For example, the system 100 illustrated in FIG. 1 includes a treatment system 102 having two permeate outlets 108. This configuration may facilitate the use of different treatment systems within a treatment system 102. For example, the treatment system 102 may include multiple filtration components, each with their own individual outlets. In some embodiments, the treatment system 102 does not separate the fluid into permeate and retentate, and the treatment system 102 does not have permeate and retentate outlets.

The vessel 110 may be a container for storing fluid. For example, fluid leaving the treatment system 102 may be deposited in the vessel 110. The fluid deposited in the vessel 110 may be held for storage, waste disposal, processing, testing, or other uses. The vessel 110 may also be a reservoir for subsequent treatment, for example, through the same treatment system 102 or a different treatment system 102. This fluid may or may not be combined with previously filtered fluid.

The treatment site 112 may contain a particular fluid to be treated. In some embodiments, the treatment site 112 may be an anatomical entity or location within a human or animal subject, such as a chamber or CSF-containing space or a blood vessel. The treatment site 112 may be the source of the fluid, the destination of the fluid, or both. For example, the system 100 may remove or receive a volume of fluid from the treatment site 112, perform treatment, and return a portion of the processed and/or treated fluid to the treatment site 112.

The various components of the system 100 may be connected through tubing 114. For instance, in certain embodiments, there may be a length of the tubing 114 placing the treatment site 112 in fluid connection with the intake 104. The permeate outlet 108 may be in fluid connection with the treatment site 112 via a length of the tubing 114. The retentate outlet 106 may be in fluid connection with the vessel 110 via a length of the tubing 114. The tubing 114 may be any kind of system for transporting or containing fluid. While the connections within the system 100 are shown as being direct, the connections need not be. The various portions of the system 100 may be connected through combinations of connections and various tubing 114. In certain embodiments, the tubing 114 and other portions of the system 100 may be filled with priming fluid (e.g., saline). Longer lengths of tubing 114 may correspondingly comprise a larger amount of priming fluid; however, in some embodiments, larger amounts of priming fluid may result in an undesirable amount of dilution of "natural" or endogenous fluid, such as CSF. Accordingly, in some embodiments, the tubing 114 may be selected to minimize the volume of priming fluid needed, while still having the system be practically useful (e.g., enough tubing to enable the system 100 to be used at a subject's bedside). Depending on the subject and the treatment site 112, the tolerance for removal or dilution of fluid may vary, and the system 100 may be scaled accordingly. For example, the parameters of the system 100 may be changed to scale to suit subjects ranging from a mouse to a human or larger mammals.

In some embodiments, the tubing 114 may have a port 124 configured to provide access to the fluid traveling within the tubing 114. As illustrated in FIG. 1, there is a port 124 between the permeate outlet 108 and the treatment site 112. This port 124 may be configured for the introduction of additives, such as therapeutic agents, artificial fluid (such as artificial CSF), and/or other additives. The port 124 may also be configured for the removal of fluid for testing or other purposes. For example, in certain embodiments, fluid returning to the treatment site 112 may be removed and tested for particular characteristics or parameters. In certain embodiments, tubing 114 that links the treatment site 112 to the intake 104 may include a port 124. This port 124 may also be used for the introduction of additives and/or the removal of fluid. In some embodiments, instead of or in addition to a port 124 located on the tubing 114, there may also be a port 122 located on the treatment system 102 itself. This port 122 may be used to access the fluid within the treatment system 102 at various points during treatment for various purposes. For example, like the port 124, the port 122 may be used to introduce additives to the system 100 or remove fluid therefrom. In some embodiments, the ports 122, 124 may be used to link the system 100 with other systems.

Figures 2, 3:
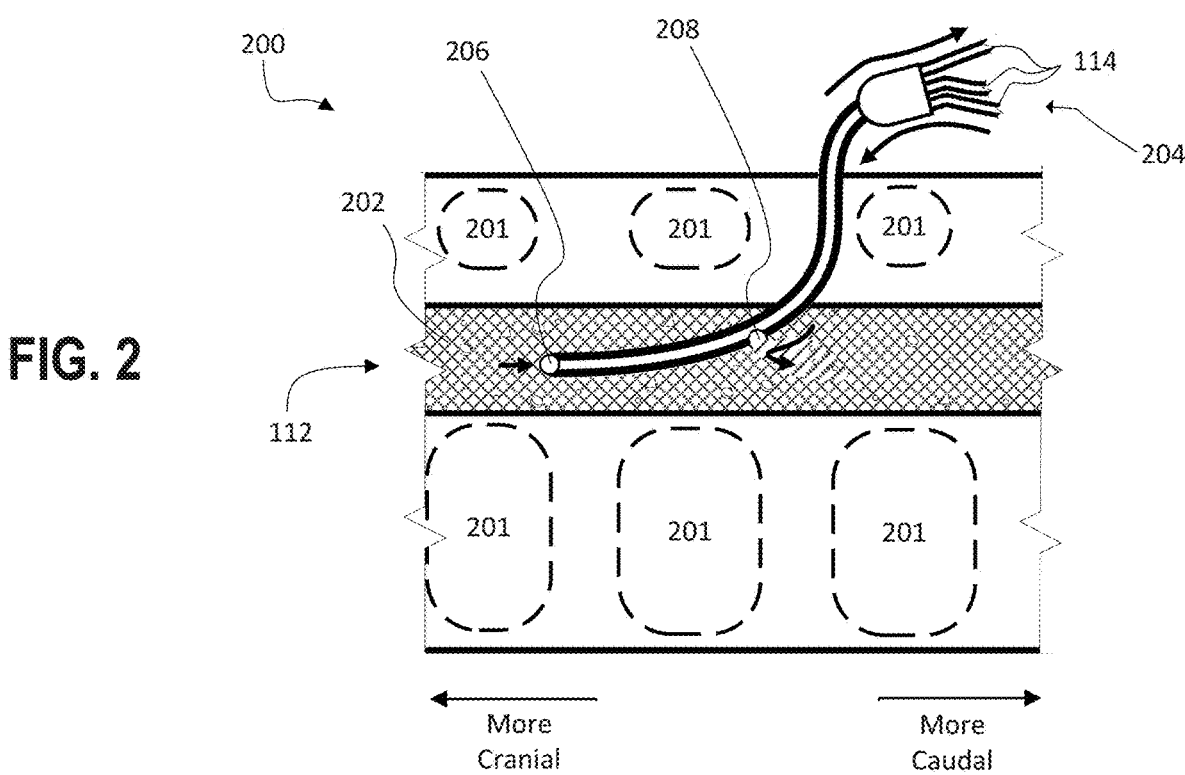
FIG. 2 illustrates fluid being withdrawn from and returned to a treatment site, according to some embodiments.
FIG. 3 illustrates fluid being withdrawn from and returned to a treatment site, according to some embodiments.

FIG. 2 illustrates a system and method for withdrawing a fluid 202 from and returning fluid to the treatment site 112, according to some embodiments. The connection between the system 100 and anatomical structures (such as the treatment site 112) may be made in a variety of ways. For example, if the treatment site 112 is an anatomical location within a subject, as shown in FIG. 2, the connection with the treatment site 112 may be made through one or more catheters inserted into particular anatomical locations. For example, the catheter may be a multi-lumen catheter inserted through a single opening in the subject to access the anatomical location or may be two catheters inserted at two different, but connected anatomical locations. In some embodiments, the connection may be made via an external ventricular drain system. For example, the tip of a catheter may be placed in a lateral ventricle of the brain.

As a specific example, the some embodiments shown in FIG. 2 include a portion of a subject's spine 200, including vertebrae 201, carrying a fluid 202 (for example, a fluid comprising CSF), and a multi-lumen catheter 204. The multi-lumen catheter 204 may comprise a first port 206 and a second port 208 that place the treatment site 112 in fluid connection with tubing 114. As illustrated, a first volume of the fluid 202 enters the multi-lumen catheter 204 through the first port 206 and is passed through into a portion of the tubing 114 (for example, a portion of tubing 114 leading to the intake 104). A second volume of fluid 202 enters the multi-lumen catheter 204 from a portion of the tubing 114 (for example, a portion of tubing 114 coming from the permeate outlet 108) and exits the multi-lumen catheter 204 through the second port 208.

The catheter 204 may, but need not, also include ports to place one or more lumens in fluid connection with the fluid 144 of the treatment site 112. The catheter 204 may be generally configured to be flexible, navigable, and atraumatic. The catheter 204 may enable sensing of temperature, intracranial pressure, and/or other parameters. The size of the catheter 204 may be approximately greater than or equal to 6 French and approximately 20 cm to approximately 120 cm to enable attachment to remote tubing (e.g. the tubing 104), a console (e.g., the treatment unit 106), or other units; however, other sizes may be used. In some embodiments, the catheter size may be approximately 5 French. Other diameters and lengths may be used, as desired.

FIG. 3 illustrates a system and method for withdrawing fluid from and returning fluid to the treatment site 112, according to some embodiments. In this particular example, tubing 114 and a muti-lumen catheter 204 are placed in fluid connection with the ventricles of a subject's brain 210. This configuration may be similar to or described as an external ventricular drain.

Although FIGS. 2 and 3 illustrate accessing CSF in a portion of the spine 200 and a portion of the brain 210, respectively, the embodiments disclosed herein need not be limited to those regions or that fluid and may be used with other locations and fluids. For example, one or more single-lumen catheters may be used to transport the fluid 202. As another example, the anatomical location may be a blood vessel and the fluid may be blood.

FIG. 4 illustrates a block diagram of a treatment system 102 according to certain embodiments, with solid arrows indicating an example flow path for fluids and materials and dashed arrows indicating an example flow path for signals and information. FIG. 4 illustrates the intake 104, the retentate outlet 106, the permeate outlet 108, a pump 222, an air trap 223, a sensor 224, a treatment unit 226, a processing unit 228, and an interface 230. Various components of the system may be selected to be fluid-contacting components or non-fluid-contacting components. Whether a component contacts the fluid may affect whether the component is disposable and the ease with which the component may be reused.

The pump 222 may be any device for inducing fluid flow through one or more portions of the treatment system 102. In certain embodiments, the pump 222 may be a peristaltic pump, which may reduce the need for sterilization of complex pump components; however, other types of pumps may be used. The operation of the pump 222 may be controlled by modifying the operating parameters of the pump 222. This may enable the flow rate, pressure, and/or other parameters of the pump 222 to be changed. The pump 222 may also be used to withdraw the fluid from the treatment site 112.

The air trap 223 can be used to facilitate priming the treatment system 102 and can be used to remove air bubbles from the system 102 to improve accuracy of the sensor 224. The air trap 223 can include a hydrophobic air vent.

The sensor 224 may be a device for generating and/or receiving information, including but not limited to one or more of characteristics of the fluid withdrawn from the treatment site 112, before, after, and/or during filtration, including but not limited to temperature; pressure; the ratio of permeate volume to retentate volume; the fluid flow rate to and/or from the treatment site 112; the amount of contaminants or other materials in the fluid; the fluid flow return rate; the filter efficiency; filter status (for example, whether the filters are clogged or otherwise running inefficiently); and other parameters or characteristics. While the sensor 224 is shown within the treatment system 102, one or more sensors 224 may be located elsewhere in the system 100 and/or cooperate with other locations. The sensor 224 may convert the data into computer- and/or human-readable representations for processing. While a single sensor is shown within the system, it will be understood that there need not be only as single sensor. Any suitable number or arrangement of sensors may be used for taking one or more readings throughout the system.

In some embodiments, the sensor 224 may be selected to or optimized for use with flow rates of approximately 0 to approximately 1200 milliliters per hour, volumes of approximately 100 to approximately 125 cubic centimeters, and pressures of approximately 0 to approximately 20 mmHg. These measurement ranges may be encountered in the system, such as in the flow rate, volume, and pressure of CSF or a heat exchange fluid. In some embodiments, the flow sensor may be accurate within a range of between approximately 0 to approximately 2400 milliliters per hour, the pressure sensor may have an effective operating range of between approximately –50 mmHg and approximately 300 mmHg. In some embodiments, sensor 224 may have a response time of approximately 20 ms. In some embodiments, the sensor 224 may be a temperature sensor configured to have an accuracy of +/−0.5° C. between approximately 4° C. and approximately 70° C. Suitable sensors may include flow sensors provided by SENSIRION of Switzerland, pressure sensors by UTAH MEDICAL of Midvale, Utah, and temperature sensors by SCILOG of Madison, Wisconsin The treatment unit 226 may be configured to treat fluid and may be one or more components of the treatment system 102. For example, in some embodiments, the treatment unit may be a device for separating a first portion of materials and/or fluid from a second portion of materials and/or fluid. The design and type of the treatment unit 226 may vary depending on the type of fluid and the desired treatment results. For example, the treatment unit 226 may include a tangential flow filter configured to separate the fluid into permeate and retentate (see, for example, FIG. 5), with the retentate flowing to the retentate outlet 106 and the permeate flowing to the permeate outlet 108. For example, various combinations of filters may be used to achieve different kinds of filtration. For example, the filters may include filters of various pore sizes and different attributes. For example, filtering schemes may include ultrafiltration, microfiltration, microfiltration and other sized filters that have various porosities. Combinations of filters may include dead end filtration, cone filters, depth filtration, tangential flow filtration, affinity filtration, centrifugal filtration, vacuum filtration, other configurations, and/or combinations thereof. Multiple treatment systems may be used to continually re-filter retentate to yield a higher volume of permeate that may be returned to the treatment site 112. In an embodiment, the filter may be configured to filter cytokines. See U.S. Pat. No. 8,435,204, previously incorporated by reference. Examples of cytokines and other proteins that may be filtered may include, but need to be limited to, EGF, Eotaxin, E-selectin, fas ligand, FGF2, Flt3 lig, fractalkine, G-CSF, GM-CSF, GRO, ICAM, IFNa2, IFNg, IL10, IL12p40, IL12p70, IL13, IL15, IL17, IL1a, IL1b, IL1ra, IL2, IL3, IL4, ILS, IL6, IL7, IL8, IL9, integrins, IP10, L-selectin, MCP1, MCP3, MDC, MIP1a, MIP1b, PDGF-AA, PDGF-AAAB, P-selectin, RANTES, sCD40L, sIL2R, TGFa, TNF, TNFb, VCAM, VEGF, and others. In some embodiments, the filter may be configured to capture and absorb cytokines in the about 10 to about 50 kDa range where most cytokines reside.

In some embodiments, the treatment unit 226 may include multiple different treatment components, including but not limited to filters, components configured to increase the performance of filters, units configured to increase the flow rate of the fluid within the treatment system 102, units configured to heat the fluid, units configured to cool the fluid, units configured to apply light treatment to the fluid, units configured to separate components of the fluid based on their dielectric properties, units configured to apply spiral separation, units configured to apply centrifugal separation, units configured to introduce additives to the fluid, units configured to target particular components of the fluid, other components, and/or combinations thereof. Some embodiments may be configured to mechanically vibrate filters in order to reduce filter clogging, improve flow, and improve reliability. Some embodiments may include an inline air trap. The inclusion of an air trap may increase performance by, for example, removing air bubbles that may otherwise be detrimental to the system by causing erroneous sensor readings and filter airlocks.

The processing unit 228 may be a device configured to control the operation of the treatment system 102, for example by sending signals to the pump 222, sensor 224, and/or treatment unit 226. In some embodiments, the signals are sent in response to receiving input from the interface 210. In certain embodiments, the processing unit 228 may process information, such as data received from the sensor 224 and/or the interface 210 and make decisions based on the information. In certain embodiments, the processing unit 228 may itself make decisions based on the information. For example, the processing unit 228 may include a processor and memory for running instructions configured to receive input, make decisions, and provide output.

The interface 230 may be a device or system of devices configured to receive input and/or provide output. In certain embodiments, the interface 230 is a keyboard, touchpad, subject monitoring device, and/or other device configured to receive input. For example, a healthcare professional may use the interface 230 to start or stop the system 100 and to modify system parameters, such as the absolute duration of the procedure, pump speed, and other parameters. The interface 230 may also include a display, speaker, or other device for sending user-detectable signals. In some embodiments, the interface 230 may comprise a network interface configured to send communications to other devices. For example, the interface 230 may enable the treatment system 102 to communicate with other treatment systems, flow control devices, a server, and/or other devices.

FIG. 5 illustrates a segment of the treatment unit 226 according to some embodiments, including a first section 256, a membrane 258, and a second section 260, with arrows indicating flow direction. As shown in FIG. 5, the treatment unit 226 is configured to include a tangential flow filter. In this configuration, the fluid 202 may enter this portion of the treatment unit 206 and pass through the first section 256. While the fluid 262 travels through the first section 256, the fluid 262 may encounter the membrane 258. A particular pressure, flow rate, or other environmental condition within the first section 256 and/or second section 260 may draw or otherwise encourage fluid to contact the membrane 258. The environmental condition may be created by, for example, the shape, size, or configuration of the treatment unit 226. The environment may also be created as a result of the pump 222 or other feature of the treatment system 102 or system 100. As a result, certain components of the fluid 262 (for example, components 252) may pass through an aperture of the membrane 258 to the second section 260. However, certain other components (for example, contaminants 254) may be improperly sized (for example, the certain other components are too large) to pass through the membrane 258 and instead remain within the first section 256. The fluid 262 that passes through the membrane 258 into the second section 260 may be described as permeate and may pass through to the permeate outlet 108.

As a specific example, the fluid 262 may be CSF having particular desirable components 252. The CSF may also contain contaminants 254, such as blood cells, blood cell fragments, hemolysis components, neutrophils, eosinophils, inflammatory cells, proteins, misfolded proteins, cytokines, bacteria, fungi, viruses, small and large molecules, oligomers (such as AP oligomers, tau oligomers, α-synuclein oligomers, and Huntingtin oligomers), antibodies (such as anti-myelin antibodies), enzymes, mutated enzymes (such as mutations to SOD1), and/or other substances. The contaminants 254 may, but need not, include materials or matter that are present in CSF normally (e.g. a cytokine that is present in CSF normally but is present in an elevated or otherwise undesirable amount). One or more of the contaminants 254 may be associated with or suspected to be associated with one or more diseases or conditions. For example, the contaminants 254 may be associated with one or more of Alzheimer's disease, Parkinson's disease, multiple sclerosis, Huntington's disease, amyotrophic lateral sclerosis, for instance, as described in U.S. application Ser. No. 13/801, 215, which was previously incorporated by reference. The treatment unit 226 may be used to separate the contaminants 254 from the fluid and/or desirable components 252 of the CSF. For instance, a membrane 258 may be sized or otherwise configured to allow CSF to flow through the membrane 258 while substantially preventing contaminants 254 from passing through the membrane 258.

Figure 6:
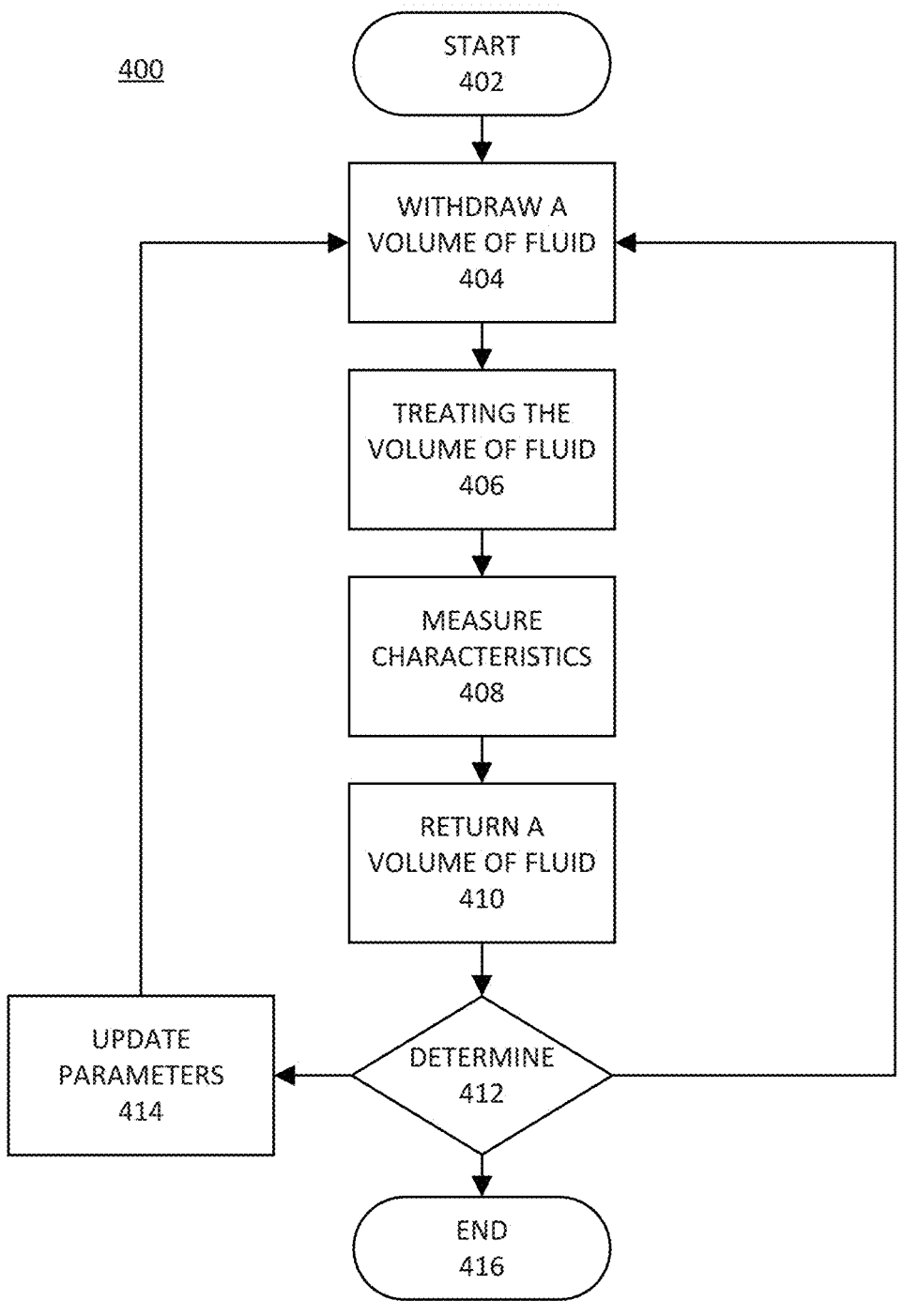
FIG. 6 illustrates a flow diagram for a method for using a treatment system for treating biologic fluids according to some embodiments.

FIG. 6 illustrates a method 400 for using a treatment system for treating biologic fluids, including the steps of starting the process 402, withdrawing a volume of fluid 404, treating the volume of fluid 406, measuring characteristics 408, returning a volume of fluid 410, determining 412, updating parameters 414, and ending the process 416. The method may be utilized with certain embodiments, including system 100. While the method will be described with reference to system 100, a person of skill in the art would be able to modify the steps to be used with other systems, including systems having a multiple treatment systems.

While the method is described as being performed on a particular volume of fluid, the system may operate on a continuous flow of fluid. That is, the system 100 need not necessarily withdraw a volume of fluid, wait for the volume to be processed and returned, and then withdraw another volume of fluid. The method may follow a continuous process. Similarly, while FIG. 6 appears to illustrate a series of consecutive steps, the steps of the described method may occur concurrently. For example, the system 100 may concurrently perform some or all of the steps illustrated in FIG. 6. For instance, the system 100 may concurrently withdraw and return fluid.

The method 400 may begin at start 402. This step 402 may include activating one or more components of the system 100. This step 402 may also include or follow various preparation steps. Such steps may include installing treatment components, selecting and preparing the treatment site 112, installing tubing 114, calibrating components, priming components of the system 100, and other steps.

The installing treatment components step may include selecting particular treatment components based on desired outcomes, the particular treatment site 112, fluid, or other considerations. For example, if the method 400 is being used on a subject suffering from a cerebral vasospasm, the goal of the procedure may be to filter blood breakdown products from the subject's CSF. This would make the treatment site 112 a lumen carrying CSF, the fluid. As such, particular treatment components would be selected to filter the blood components from the CSF. For example, a membrane 258 with apertures sized to substantially prevent the flow of blood components, while large enough to substantially allow the entry of CSF as permeate, may be used.

As another example, if the method 400 is being used on a subject suffering from or suspected to be suffering from cyptococcal meningitis, the goal of the procedure may be to remove or inactivate Cryptococcus neoformans fungi that may be within the subject's CSF. The treatment site 112 may then be a lumen carrying CSF and treatment components may be selected to heat the CSF to inactivate the fungi and then filter the fungi from the CSF.

The selecting and preparing the treatment site 112 step may include choosing a particular treatment site 112. For example, a healthcare professional may select an individual who may benefit from having treatment performed on a bodily fluid and identify a reservoir containing the fluid. This may include, as described above, a subject suffering from a cerebral vasospasm. Preparing the treatment site 112 may include identifying an anatomical location for a procedure to access the treatment site 112 (for example, in a spinal portion 200, as shown in FIG. 2), sterilizing the location, or otherwise preparing the treatment site 112 for the procedure. Selecting and preparing the treatment site 112 may be performed according to the systems and methods described within this application or through other means. For example, selecting and preparing the treatment site 112 may be performed according to the various systems and methods described in U.S. patent application Ser. No. 14/743,652, which was previously incorporated by reference.

Installing tubing 114 may include connecting various components of the system 100. For example, retentate outlet 106 may be connected to flow regulator 118. This step may also include installing tubing 114 to withdraw fluid from and return fluid to the treatment site 112. This step may include inserting a multi-lumen catheter into an anatomical location to place the treatment site 112 in fluid connection with the system 100 to enable fluid to be drawn into the intake 104 and returned to the treatment site 112.

Calibrating components may include setting initial parameters for the use of the system 100. This step may include establishing an initial flow rate, an initial pressure, and other initial parameters or system settings. The initial parameters may be based on observed or predicted clinical measures, including but not limited to an estimated amount of fluid in the treatment site 112, the health of the subject, the predicted ratio of retentate to permeate, and other factors.

Priming the system 100 may include adding a priming solution to one or more of the components of the system 100. Depending on the configuration of the system 100, priming may be necessary for one or more components to function effectively. Depending on the treatment site 112, fluid, and the subject, priming may be necessary to assure comfort or good health. In certain applications, the system 100 may be primed to enable the return of a volume of fluid while simultaneously withdrawing a volume of fluid. This may be especially useful for applications where the treatment site 112 has a relatively small volume of fluid (e.g., during filtration of CSF) or is otherwise sensitive to relative changes in volume. Depending on the type of filtration being used, the length of the procedure, and other factors, priming fluid may be added during the filtration procedure to make up for fluid lost during the procedure At step 404, a volume of fluid is withdrawn from the treatment site 112. In certain circumstances, the fluid may be withdrawn using a pump or device located within the system 100. For example, the pump may be a component of one or more of the flow regulators 118; the treatment system 102 (such as pump 222); and/or the combiner 116. The pump may be used to withdraw a volume of fluid from the treatment site 112.

In some embodiments, the rate at which the fluid is withdrawn from the treatment site 112 is between approximately 0.01 mL/min and approximately 100 mL/min, between approximately 0.04 mL/min and approximately 30 mL/min, between approximately 0.1 mL/min and approximately 10 mL/min, or in other ranges. However, the amount withdrawn may be higher or lower depending on the application. The amount may vary depending on various factors including but not limited to the type of fluid being withdrawn, the viscosity of the fluid, the amount of fluid in the treatment site 112, and other factors. The viscosity of the fluid may vary over time, and depending on the particular subject. For example, the viscosity of CSF may be different in a subject with meningitis than a subject with typical CSF.

Once the fluid is withdrawn from the treatment site 112, the fluid may pass through the tubing 114 and into the treatment system 102 via intake 104.

At step 406, the volume of fluid is treated. This may include the steps of passing the fluid through the treatment unit 226 of the treatment system 102. While the fluid passes through the treatment unit 226, it may pass through multiple different components to treat the fluid. For example, the fluid may be heat treated using a heating unit and then filtered using a filtration unit. As another example, the fluid may pass through various filtration components including but not limited to tangential flow filtration, microfiltration, ultrafiltration, nanofiltration, dead-end filters, depth filters, and other filtration devices or mechanisms.

The treatment process may result in the separation of the fluid into a retentate flow and a permeate flow. The permeate flow may leave the treatment system 102 through a permeate outlet 108 and the retentate may leave the treatment system 102 through a retentate outlet 106. Depending on the configuration of the filters and the goals of the method 400, in some implementations, the permeate may be the fluid to be returned to the treatment site 112. In other implementations, the retentate may be returned to the treatment site 112. The retentate may be a fluid that contains contaminants or is otherwise in a condition undesirable for returning to the treatment site 112.

In certain embodiments the retentate may be successively or progressively treated, such as by being treated again through another treatment process or by being treated again through the same treatment system 102 by being redirected through it. For example, in some embodiments, the retentate may be passed through a flow regulator and into treatment system 102 for additional filtration. The permeate may flow from the permeate outlet 108 to a combiner for return to the treatment site 112. The second retentate may be treated further. Once the fluid is sufficiently treated, the remaining retentate or contaminants may be passed through a flow regulator and into a vessel 110 for analysis, disposal, storage, or other use, or, alternatively, or in addition, the remaining retentate may be subjected to further processing, treatment, and/or filtration (any number of times), where the further treated fluid is, for example, directed to treatment site 112, either directly or in combination with other fluids.

At step 408, characteristics of the fluid and/or the system may be measured. Measuring characteristics may include intermittent or continuous sampling and/or monitoring of characteristics or parameters of interest. While this step 408 is shown as occurring after the treatment of the fluid 406, the step 408 may take place at any point during the process 400 where useful data may be gathered.

In certain embodiments, measuring characteristics may include measuring the characteristics of the fluid withdrawn from the treatment site 112 before, during, or after treatment. The characteristics measured may include the presence or amount of particular contaminants, proteins, compounds, markers, and other fluid components present. As another example, the ratio of permeate volume to retentate volume, the fluid flow rate from the treatment site 112, fluid temperature, fluid opacity or translucency or transparency, an absolute retentate flow rate, and the rate of fluid flow to the treatment site 112 also may be measured. The performance characteristics of the system 100 may also be measured. For example, the efficiency of the treatment unit 226, the status of the treatment unit 226 (for example, via the interface 210), and other markers of system 100 performance.

Data utilized by the system need not be limited to directly or actually measured data. Data may be inferred from actually measured data. For example, retentate flow rate may be determined using a difference between a pump rate and a permeate rate. This method would allow the system to measure a value that may be unmeasurable, difficult to measure, or inaccurate due to, for example, changing viscosity.

In certain embodiments, the characteristics measured may include information about a subject or input by a healthcare provider. For example, the system 100 may monitor the blood pressure, heart rate, stress, and other information of the subject. In addition to quantitative characteristics, qualitative measurements may be made as well. For instance, subject discomfort and other qualities may be measured. These and other data may be measured by the sensor 224 and/or be input into the system by an input device (for example, keyboard, touch screen, subject-monitoring device, and other devices for receiving input) operably coupled to the system 100.

At step 410, a volume of fluid is returned to the treatment site 112. In certain embodiments, the fluid is returned to the treatment site 112 as soon as fluid treatment has been completed. In certain embodiments, the flow rate of the fluid may be controlled. For example, a volume of fluid may be buffered at the combiner 116 or in another area of the system 100 for a time before being returned to the treatment site 112. Buffering may be used to smooth the return rate of the fluid, to allow time for the fluid to reach a particular temperature, to allow time for a particular additive to mix within the fluid, and for other reasons.

In certain embodiments, the rate and/or pressure at which the fluid is returned to the treatment site 112 is controlled so that the fluid is returned at such a rate or in such a manner as to maintain homeostasis within the treatment site 112. In certain embodiments, this may be accomplished by returning fluid at the same rate at which fluid is currently being withdrawn from the system. In certain embodiments, the fluid may be returned at substantially the same flow rate at which it was removed. The fluid volume removed from the system and returned to the system may not be equal. This may be the case when removing a significant quantity of contaminants from a treatment site. In certain embodiments, the difference may be made up through the addition of a secondary fluid or via the body's natural production.

In certain embodiments, a particular volume of additional fluid may be returned to the treatment site 112. The additional fluid may be fluid that was not withdrawn from the treatment site 112, previously withdrawn from the treatment site 112, withdrawn from a different treatment site, synthetically created, naturally created within the subject's body, or is otherwise different from the volume removed from the treatment site 112 in step 404. The return of additional fluid may be used to, for example, compensate for the volume of fluid that was filtered out, especially in circumstances where the treatment site 112 comprised only a small amount of fluid at the start 402.

In certain embodiments, one or more therapeutic agents may be added to the fluid prior to its return to the treatment site 112. The fluid may be treated or mixed with a particular pharmacological agent. For example, when the fluid is CSF, the agent may be configured to bypass the blood-brain barrier. The agents may include, but need not be limited to, antibiotics, nerve growth factor, anti-inflammatory agents, pain-relief agents, agents designed to be delivered using intrathecal means, agents designed to affect a particular condition (e.g., meningitis, Alzheimer's disease, depression, chronic pain, and other conditions), and other agents.

As a specific example, the treatment site 112 may be a CSF-containing space of a subject, such as the subarachnoid space or another space known or thought to contain CSF. The space may only have a total of approximately 125 ml of CSF, and if the level drops below a certain threshold (for example, approximately 85 ml), the subject may suffer undesirable side effects. If a particular large amount of the existing CSF comprises undesirable compounds, the volume of permeate may be small enough to cause the fluid levels in the treatment site 112 to drop below the threshold. Consequently, the system 100 may return a volume of additional fluid (for example, artificial CSF or other suitable fluid) to adjust for the difference between the amount of withdrawn CSF being returned and the amount needed to be returned to maintain the volume of the treatment site 112 above the threshold amount.

In certain embodiments, the withdrawal and return of the fluid may occur in a pulsed manner. For example, the system 100 may withdraw a particular volume and then cease withdrawing additional fluid. The withdrawn volume is treated and buffered (for example, at a combiner). An amount of the treated fluid from the buffer may be returned to the treatment site 112 at about the same rate and/or for the about same total volume as a next volume is withdrawn from the treatment site 112. This process may allow the system to maintain treatment site 112 volume levels relatively consistent and may be useful in circumstances where the processing time (for example, the time between the fluid being withdrawn from and returned to the treatment site 112) is long.

At step 412, a determination is made. The determination may be made by, for example, a healthcare professional, a processor system, or a combination thereof. For example, the healthcare professional may analyze the measured characteristics and come to a conclusion. As another example, the processing unit 208 may analyze the measured characteristics using an algorithm or through other mechanisms. The determination may be based on the measured parameters, a timer, a schedule, or other mechanisms. The determination may be used to change the parameters of the system 100, may change over time, and may address particular measured characteristics.

For example, a determination may be made regarding the flow rate at which the fluid is being withdrawn and/or returned to the treatment site 112. For example, it may be desirable to maintain substantially the same withdrawal and return rate of the fluid. Specifically, if more fluid is being withdrawn from the treatment site 112 than is being returned, then the volume of fluid in the treatment site 112 may be decreasing overall. This may be undesirable because for certain fluids and certain treatment sites 112, if the volume of the treatment site 112 passes a particular threshold, undesirable side effects may occur. For instance, where the fluid being withdrawn is CSF, the flow rate may be such that the volume of CSF removed from a human subject does not exceed about between approximately 5 mL and approximately 20 mL over the course of one hour. That is, the volume of fluid does not decrease more than approximately 5 mL to approximately 20 mL from its original starting volume in a one hour period of time. In certain embodiments, it may be desirable to maintain an absolute retentate flow rate within a certain range of acceptable retentate flow rates. In certain embodiments, the threshold may be between approximately 0.10 mL/min and approximately 0.30 mL/min. In certain embodiments, the threshold may be approximately 0.16 mL/min. In certain embodiments, the threshold may be between approximately 0.2 mL/min and approximately 0.25 mL/min; however, other values may be desirable in certain circumstances. In certain embodiments, a pump may be running at approximately 1.0 mL/min and the retentate flow rate is approximately 0.25 mL/min, the permeate flow rate is approximately 0.75 mL/min, which is about a 3:1 ratio. However, if the pump speed were increased to approximately 2.0 mL/min, the retentate flow rate may be held at approximately 0.25 mL/min, which leaves the permeate flow rate as approximately 1.75 mL/min, or about a 7:1 ratio. By maintaining the retentate flow rate within the threshold, the system may be considering functioning as intended, despite the change in ratios.

Based on the measured characteristics, it may be determined that the best way to address the disparity in the withdrawal and return rates may be to decrease the flow rate to reduce the overall volume of fluid lost from the system. This may mean that, although there is a net loss of fluid from the treatment site 112, the loss is occurring at a slower rate. The rate may be sufficiently slow that, for example, that the subject's body produces sufficient fluid to make up for the loss.

For example, at the beginning of the filtration process 400, the fluid may contain large amounts of contaminants, resulting in a comparatively large amount of material being filtered out and a comparatively small amount of the fluid being returned (for example, permeate). As the filtration or treatment process continues, the amount of fluid being treated may decrease because the contaminants have already been filtered out (for example, retentate). In this scenario, a determination may be made to begin the process at a relatively low flow rate and then increase it as the volume of the fluid being filtered out decreases. In addition, the determination may include altering the flow and/or pressure within the treatment unit 226 to achieve particular filtering results.

As another example, the measured characteristics may be a subject's expressed discomfort. Withdrawing CSF from a CSF-containing space of a subject may cause symptoms of overdrainage, such as spinal headache. Symptoms of overdrainage may be able to be avoided or otherwise addressed by not withdrawing more than a threshold amount of CSF. However, the particular threshold may vary from subject to subject. As such, a predicted threshold may be different from an actual threshold and the subject may experience symptoms sooner than expected. In response to the subject expressing feelings of discomfort, the healthcare professional may determine that the parameters of the process may need to be changed.

In some embodiments, a system may predict the occurrence of a spinal headache or a hemorrhage based on the amount of CSF removed from the subject and/or the subject's intracranial pressure. The system may be configured to modify treatment parameters responsive to detecting that a threshold amount of CSF was removed or a threshold intracranial pressure was reached. For example, the threshold amount may be an amount of CSF removed, an amount of CSF removed over a period of time, or an intracranial pressure predicted to induce spinal headache. In some embodiments, the threshold amount of CSF removed or the threshold amount of CSF removed over a period of time, may be within about 100% to about 50%, about 95%, about 90%, about 85%, or about 80% of the amount predicted to cause a spinal headache. In some embodiments, the threshold amount may be less than about 300% to about 100%, about 150%, about 125%, about 110%, about 105%, or about 100% of the amount of intracranial pressure predicted to cause a spinal headache. In some embodiments, the predicted volume of removed CSF (without replacement) that is sufficient to induce a spinal headache is an amount greater than 15 milliliters per hour.

In certain embodiments, at step 412, the processing unit 228 and/or a healthcare professional may determine that the process should be completed. At this point, the flow diagram moves to end step 416. In certain other embodiments, at step 412, the processing unit 228 and/or a healthcare professional may determine that the process should continue substantially unchanged. Upon that determination, the flow diagram may return to step 404. In still other embodiments, at step 412, the processing unit 228 and/or a healthcare professional may determine that the one or more parameters of the process should be changed. Upon that determination, the flow diagram may move to step 414.

At step 414, one or more parameters of the system 100 are changed in response to a determination made in step 412. The parameters to be changed may include inflow rate, outflow rate, buffer size, and other parameters. Such parameters may be changed via, for example, the processing unit 206 sending a signal to the pump 222 or other component of the system to modify the parameters. In certain embodiments, the parameters may be manually changed through input received at the input 208. This may include parameters entered by a healthcare professional. In certain embodiments, parameters may be updated based on the difference between the withdrawal volume and the returned volume (e.g., a waste rate).

In certain embodiments, the updating parameters step 414 may include changing the flow direction of the fluid. For example, a system may include a plurality of treatment systems, which the fluid may be directed to by the manipulation of a valve or other mechanisms for changing fluid flow direction. Step 414 may include changing the fluid flow from one treatment system to a different treatment system. This may be in response to determining that a second treatment system is more suited for particular treatments than a first treatment system.

In certain embodiments, the updating parameters step 414 may include modifying the positioning of the tubing at the treatment site 112. For example, one or more inflow or outflow tubes 114 may become clogged or otherwise be operating at a reduced capacity. In response, the tubing 114 may be adjusted or otherwise modified to address the reduced capacity issue. The healthcare professional may be alerted to the issue by a light, alarm or other indicia.

In certain embodiments, the updating parameters step 414 may include cleaning or otherwise modifying one or more components of the system 100, such as the treatment unit 226. This may be accomplished by, for example, changing back pressure and pump speed.

In certain embodiments, the updating parameters step 414 may include sensing characteristics of the system to determine whether the treatment unit 226 or other components of the system are experiencing clogging. The sensed characteristic may include reading an alert state of the treatment system or detecting an increase in filter pressure with no change to system flow rates or other parameters of the system. Responsive to determining that there may be a clog in the system 100, the flow rate through the retentate port of the filters may be increased. The increased flow rate may be the result of a user or the system opening a back pressure valve (e.g., a backpressure valve of the flow regulator 118). The opening of the valve may result in a surge of fluid through one or more retentate ports of one or more filters into a waste collection area (e.g., vessel 110). The surge of fluid may result in the flow returning to the treatment site

112 reducing to zero or even a negative rate. Thus, the operator or system controlling the flow rate may take into account the volume of fluid lost and the possible effects on the patient as a result of this filter clearance mechanism.

At step 416, the process comes to an end. After the process is completed, various wind-up steps may be performed, including but not limited to, applying a bandage to the subject, disassembling one or more components of the system 100, analyzing an amount of the withdrawn fluid, analyzing the retentate, and other steps.

Increasing the Performance of Filtration Systems

In some embodiments, the performance of a filtration system, such as tangential flow filtration systems, may be improved by heating the CSF to a target temperature, cooling the CSF to a target temperature, increasing CSF flow rate, applying light treatment to the CSF, separating cells via their dielectric properties, applying spiral and/or centrifugal separation, binding additives to target particles, applying combinations thereof, or other techniques.

Heating or Cooling CSF to a Target Temperature

In some embodiments, heating or cooling CSF to a target temperature may improve performance of a filtration system and provide other beneficial results. For example, heating or cooling CSF to a target temperature may affect microorganisms or other components of CSF. In particular, heating or cooling the CSF may inhibit microorganisms within the CSF. Inhibiting microorganisms may include impairing the ability of the microorganism to reproduce, preventing the microorganism from being able to reproduce, killing the microorganism, inactivating the microorganisms, attenuating the microorganisms, or otherwise decreasing the potential negative effects of the microorganism. For a system or process to inhibit microorganisms, it need not inhibit all microorganisms. For example, the system may inhibit about 50%, about 60%, about 70%, about 80%, about 90%, about 95%, about 99%, about 99.9%, about 99.99%, more than 99.99%, or another percentage of all microorganisms.

In addition to causing disease, microorganisms may reduce the effectiveness of CSF treatment systems. Reproducing fungi, viruses, and/or bacteria may clog a filter or other parts of the treatment system 100. Once a few microorganisms are on a filter, then they may continue to multiply and cover the entire filter. Further, once the microorganisms become lodged in a portion of the system, that portion may become a continuing reservoir of pathogens. One solution is to alter the temperature of the CSF to kill or inhibit the microorganisms.

The target microorganism may be a fungus such as *Cryptococcus neoformans* or *Cryptococcus gattii*, fungi responsible for cryptococcal meningitis. *C. neoformans* thrives in environments that are warm, such as 37° C., typical human body temperature. The ability of *C. neoformans* to thrive at this temperature makes it particularly deadly for people with immune compromised systems. However, *C. neoformans* has a maximum growth temperature of approximately 40° C. See, John R. Perfect, *Cryptococcus neoformans*: the Yeast that Likes It Hot, 6 FEMS YEAST RES 463-468 (2006), hereby fully incorporated by reference for any and all purposes as if set forth herein in its entirety. See also, A. Madeira-Lopes, et al., Comparative study of the temperature profiles of growth and death of the pathogenic yeast *Cryptococcus neoformans* and the non-pathogenic *Cryptococcus albidus*, J. BASIC MICROBIOL. 26 (1986) 43-47, hereby fully incorporated by reference for any and all purposes as if set forth herein in its entirety. Accordingly, heating CSF to a temperature of 40° C. or higher may kill or inhibit the growth of certain fungi, such as *C.*

*neoformans*. Heating may be used to target other microorganisms or components of CSF as well.

Like treating CSF with heat, cooling the CSF may impair the survivability of microorganisms. For example, cooling CSF may prevent or inhibit microorganisms from reproducing, thus reducing the likelihood of the microorganism clogging the treatment system 102 or otherwise reducing performance of the system 102. Some embodiments may be configured to cool CSF to a target temperature to precipitate out certain proteins and/or slow or stop reproduction of a target microorganism. The CSF may be cooled to a target temperature at which a target protein precipitates out of the solution. Proteins precipitate out of a solution once the protein reaches a certain temperature. In particular, proteins may be soluble in solution but become folded solid as they are cooled. The temperature at which the protein precipitates out may vary based on the target protein.

Figure 7:
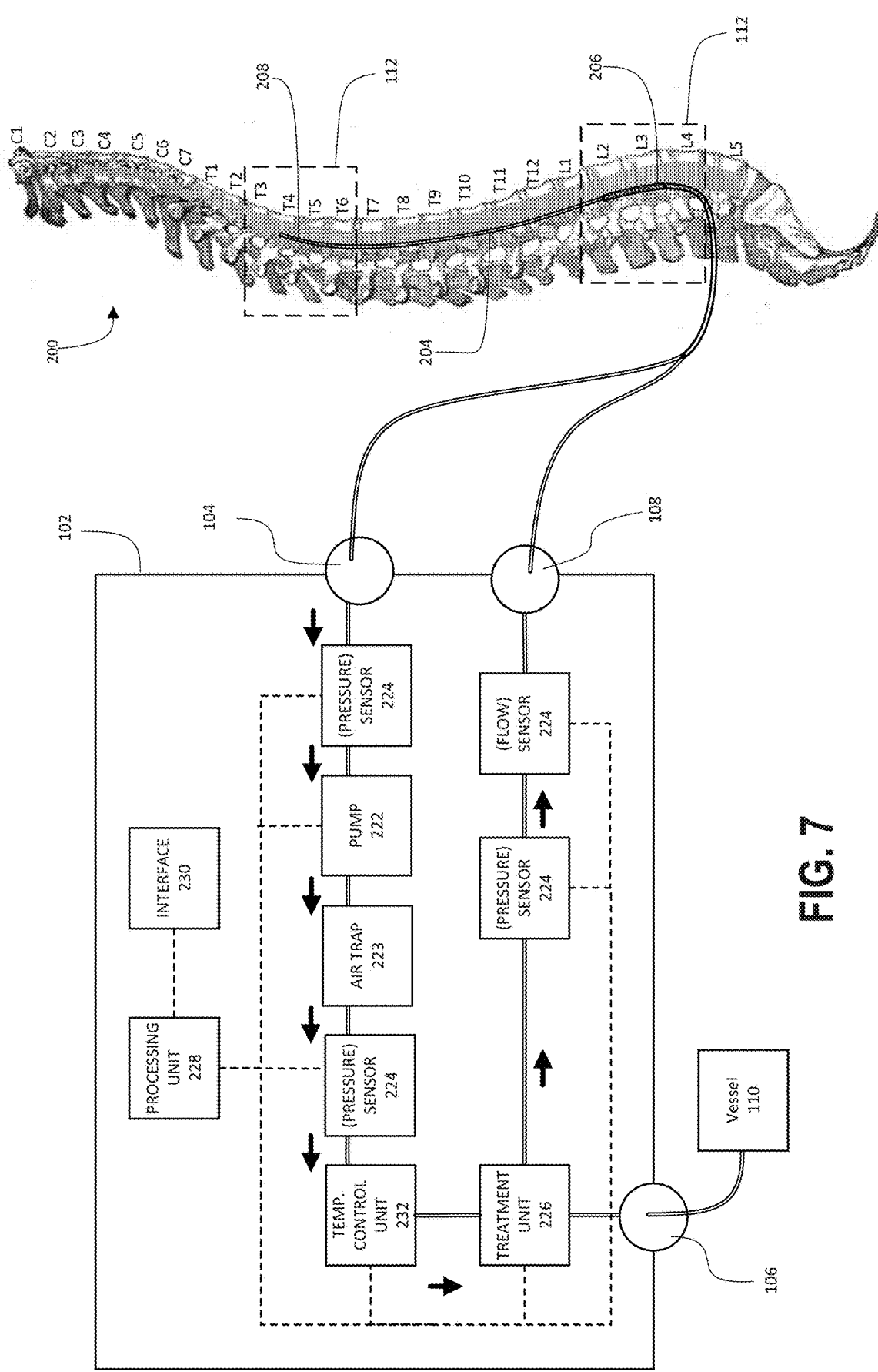
FIG. 7 illustrates systems and methods for treating CSF by altering the temperature of the CSF and filtering the CSF according to some embodiments

FIG. 7 illustrates systems and methods for withdrawing CSF, altering the temperature of the CSF, filtering or otherwise conditioning the CSF, and returning the CSF in a spinal region according some embodiments. These systems and methods may be controlled and monitored by a processing unit 228 and/or an interface 230. These components 228,230 may be connected to the other components of a treatment unit 102. The systems and methods may include the withdrawal and return of CSF from treatment sites 112 using first ports 206 and second ports 208, respectively. The treatment cycle may begin with the withdrawal of CSF from a lumbar cistern treatment site 112 using the first port 206 and an elongate catheter 204. The catheter 204 may be deployed such that the first port 206 is located within the target lumbar cistern treatment site 112 and the second port 208 is located within a target mid-to-upper thoracic treatment site 112. The target lumbar cistern treatment site 112 may be located in a region near or between the L2 and L4 vertebrae, in a region near or between the T12 and T10 vertebrae, or in other locations. The target mid-to-upper thoracic treatment site 112 may be located in a region near or between the T6 and T3 vertebrae, in a region near or between the T8 and T4 vertebrae between the C7 and T4 vertebrae, or in other locations though other locations may be used.

As the CSF is withdrawn from the target lumbar cistern treatment site 112, the CSF passes through an inlet lumen of the catheter 204 and enters the treatment system 102 through the intake 104. Next, a sensor 224 may read the pressure of the CSF as the CSF passes through a pump 222 and an air trap 223. The pressure of the CSF is taken again using a sensor 224 as the fluid moves through a temperature control unit 232.

The temperature control unit 232 may be a unit configured to cool or heat fluid as needed to reach a target temperature. The heating system may include various sensors and feedback loops to control the temperature. Various cooling techniques may be used, including but not limited to vapor-compression, thermoelectric cooling, radiator, cool bath, other techniques, or combinations thereof. Various heating techniques may be used, including but not limited to heating coils, warm baths, other techniques, or combinations thereof. While the temperature control unit 232 is illustrated as located within the treatment system 102, it may be located elsewhere within the system 100 as a whole. For example, the temperature control unit may be located external to the treatment system 102. In some embodiments, the temperature control unit 232 does not cool or warm the CSF directly and instead cools or warms a heat transfer fluid that is circulated to warm or cool the CSF. In other embodiments, the temperature control unit 232 cools or warms a filter of the treatment unit 226 itself.

The temperature control unit 232 may modify the temperature of the withdrawn CSF. For example, the temperature control unit 232 may cool or warm the CSF. After the CSF leaves the temperature control unit 232 (or is otherwise cooled), the CSF may be filtered using a filter of the treatment unit 226. In some embodiments, the CSF may be filtered before its temperature is modified. The treatment unit 226 may separate the CSF into permeate and retentate. The retentate may pass through the retentate outlet 106 and deposited in a vessel 110 for disposal or additional processing. The permeate may pass a pressure control sensor 224 and a flow rate sensor 224. Next, the permeate passes through the permeate outlet 108 and an outlet lumen of the catheter 204. The permeate then leaves the catheter 204 through the second port 208 and is deposited in the cervicothoracic junction treatment site 112.

The heating or cooling of the CSF may, but need not, be rapid. The system may be configured to alter the temperature of the CSF so the CSF reaches a target temperature by the time the CSF reaches a filter of the treatment unit 226. The target temperature may be a temperature above or below a temperature which target microorganisms (or a percentage thereof) reproduce and/or survive. For example, the temperature may be a temperature above which about 50%, about 75%, about 90%, about 99%, or about 99.9% of target microorganisms are unable to reproduce or survive.

The target temperature may also be a temperature below or above which the CSF is damaged or the proteins of the CSF are denatured. For example, albumin, which constitutes about 35% to about 80% of total protein in CSF, may be treated at 60° C. without being damaged. Ribonuclease (pH 2.0) may denature at about 30° C., ubiquitin (pH 4.0) may denature at about 82° C., and staphylococcal nuclease (pH 6.5) may denature at about 38° C. See Cristiano L. Dias, et al., The hydrophobic effect and its role in cold denaturation, 60 CRYOBIOLOGY 91-99 (2010), incorporated herein by reference for any and all purposes as if set forth herein in its entirety. In some embodiments, there may be an acceptable amount of denaturation of or damage to the CSF by heating. For example, the benefit to the subject by heating to the CSF to a target temperature to kill a target microorganism may outweigh a detriment caused by denaturing some of the CSF's albumin. In some embodiments, the system may include a treatment system configured to capture denatured proteins to reduce the amount of denatured proteins returning to the subject.

In some embodiments, the target temperature may be about 47° C. or about 45° C. In some embodiments, the target temperature may be about 37° C. to about 90° C., about 40° C. to about 80° C., about 45° C. to about 65° C., about 45° C. to about 60° C., about 45° C. to about 55° C., or about 50° C. In some embodiments, the target temperature may be a temperature above which a target microorganism reproduces and/or survives. For example, thermal death of *C. neoformans* begins at temperatures above 40° C. and increases rapidly as the temperature approaches 45° C. Accordingly, the temperature of the CSF may be increased within this range, or higher, to target *C. neoformans*. In some embodiments, the system may be configured to cool the CSF so the CSF reaches a target temperature by the time the CSF reaches a filter of the treatment unit 226. The target temperature may be a temperature below which a target microorganism reproduces and/or survives. In some embodiments, the target temperature may be below about 37° C., below about 30° C., below about 20° C., and/or below about 10° C. The system 100 may be configured to maintain the CSF at or near the target temperature for about 1 second to about 10 seconds or about 5 seconds. Other time ranges may be used as well. For example, about 1 second to about 10 minutes or about 5 seconds to about 5 minutes.

In some embodiments, the target may be a target protein that is the first or one of the first proteins to precipitate out of the CSF. This property of the target protein may enable it to be targeted for filtration or special processing. For example, the target protein may be precipitated out and then subject to special treatment (e.g., filtration, disposal, or other treatments). In some embodiments, the precipitated protein is added back to the solution.

In embodiments that warm the CSF, the system may be configured to allow the CSF to cool to about 37° C. or cooler before it is returned to the subject. In some embodiments, the CSF may cool quickly over short lengths of tubing. For example, in approximately six inches of tubing CSF flowing at a rate of at approximately one milliliter a minute may be cool from about 39° C. to about 22° C. In some embodiments, the tubing through which the treated CSF passes may be submerged in a cool bath to lower the temperature of the CSF. In other embodiments, the CSF may pass through a radiator or other cooling system. In embodiments that cool the CSF, the cooled CSF may be warmed or be allowed to warm before returning to the subject. It may also be beneficial to maintain the CSF in a cooled state as it is returned to the subject or otherwise cool the subject. Such benefits and techniques are described in U.S. patent application Ser. No. 15/287,174, entitled "Devices and Methods for Providing Focal Cooling to the Brain and Spinal Cord", which was previously incorporated by reference. These benefits include inducing hypothermia, which can have neuroprotective effects.

Applying Light Treatment to the CSF

Some embodiments may utilize light to treat CSF. For example, ultraviolet (UV) light may be applied to the CSF in order to treat targets. As another example, photodynamic therapy may be used to treat targets.

Figure 8:
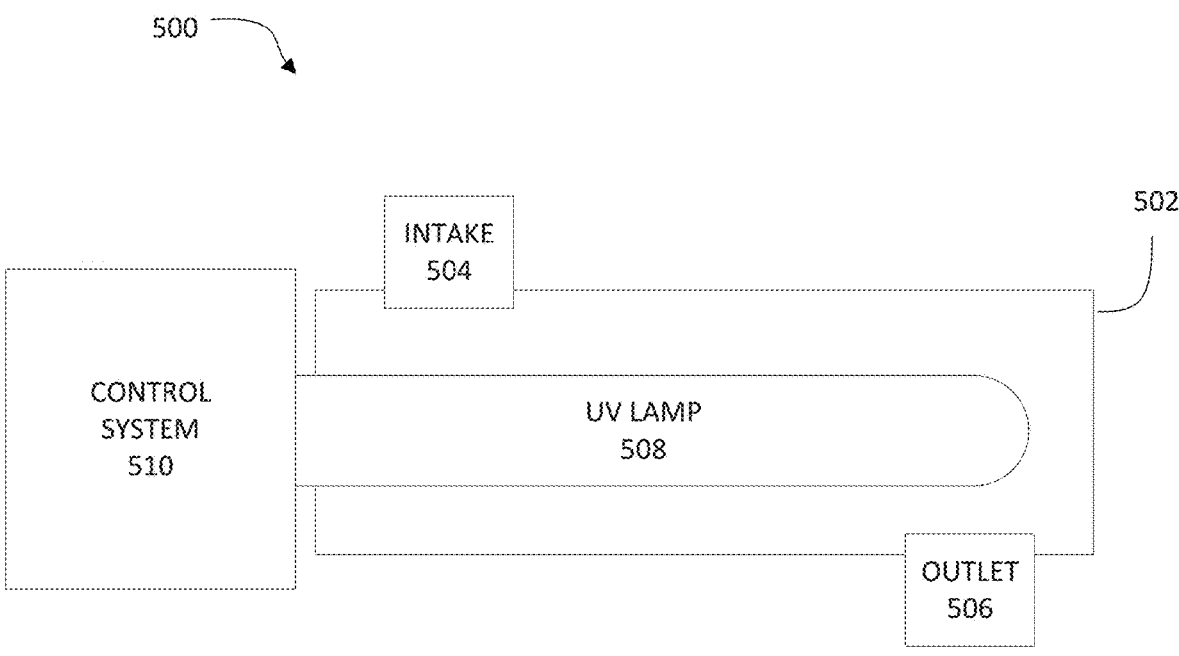
FIG. 8 illustrates systems and methods for treating CSF with ultraviolet light according to some embodiments.

FIG. 8 illustrates systems and methods for treating CSF with UV light according to some embodiments. The UV light treatment may be applied extracorporeally or via a catheter disposed within the subject. Systems and methods used to treat withdrawn CSF with UV light may be similar to the systems and methods shown in FIG. 7 that change the temperature of CSF. For example, in addition to or instead of the temperature control unit 232, the treatment system 102 may include a UV treatment system 500. The UV treatment system 500 may include a UV reactor 502, in which CSF may flow from an intake 504 to an outlet 506. Disposed within the UV reactor 502 and within the flow path of the CSF is a UV lamp 508. The UV lamp 508 is configured to provide UV light within the UV reactor 502 to treat the CSF flowing therein. The particular wavelength of UV light may be selected to improve the treatment qualities of the UV light. In particular, wavelengths in the range of about 270 nm to about 250 nm may be used to effectively inactivate microorganisms. The UV lamp 508 may be controlled by a control system 510. The control system 510 may include components for controlling the operation of the UV lamp 508 and may interact with other components of the treatment system 102, such as the processing unit 228 and the interface 230. The system 500 may also be include various thermal insulation or UV shielding or other protective elements to avoid undesirable exposure to the UV radiation and to avoid undesirable heating of the CSF or components of the system 100 from the UV lamp. In some embodiments, the thermal insulation may be partially or entirely omitted so as to cause the heating of the CSF. This may be used to cause heat treatment of the CSF, as previously described. Other systems or methods of applying UV light may be used, including but not limited to systems in which the UV lamp 508 is not disposed within a flow path of the CSF and is instead isolated from the flow of CSF.

The UV treatment system 500 may be configured to inactivate germs within the CSF. The dose of the UV treatment applied to the CSF may be a function of the intensity of the UV light and the time over which the UV light is applied to the CSF. For example, the dose may be described in terms of millijoules per square centimeter. A dose may be selected to inactivate about 99.9% of microorganisms. Such a dose may vary depending on the particular microorganism. See Gabriel Chevrefils, et al., UV Dose Required to Achieve Incremental Log Inactivation of Bacteria, Protozoa and Viruses, IUVA NEWS, vol. 8, no. 1, p. 38-45 (March 2006), incorporated by reference herein for any and all purposes as if set forth herein in its entirety. For example, a UV dose to inactivate *staphylococcus* may be in the range of about 3 mJ/cm$^2$ to about 8 mJ/cm$^2$. Typical doses to inactivate bacteria may be in the range of about 2 mJ/cm$^2$ to about 16 mJ/cm$^2$. Typical doses to inactivate viruses may be about 4 mJ/cm$^2$ to about 40 mJ/cm$^2$. The wavelength of the UV light may be in the about 400 nm to about 100 nm range. A dose may be selected to inactivate a smaller percentage of microorganism, such as about 50%, about 75%, about 90%, about 95%, or other percentages. A dose may be selected to achieve a particular log reduction in the number of live germs, such as about a 1 log, 2 log, 3 log, 4 log, 5 log, 6 log, 7 log, or other log reduction. In some embodiments, reactor 502 may be configured such that CSF flowing through the reactor 502 may receive a particular dose of light. This may be accomplished by, for example, lengthening or shortening the fluid flow path and/or increase or decreasing the fluid flow speed of the CSF through the reactor 502.

In some embodiments, a method for treating the CSF with UV light may involve withdrawing a volume of CSF, applying a germicidal dose of UV light to the CSF, filtering the treated CSF, and returning the CSF to the subject. Withdrawing and returning the CSF may be performed according to various methods and systems described herein.

In some embodiments, photodynamic therapy may be used to treat targets. Photodynamic therapy may involve activating photosensitive substances with light. See Renato Prates, et al., Photodynamic therapy can kill *Cryptococcus neoformans* in in vitro and in vivo models, PROC. OF SPIE, vol. 7165 (2009), incorporated by reference as if set forth herein in its entirety. The photosensitive substance may be a target within the CSF, such as a virus, bacteria, or fungi. In some embodiments, the photosensitive substance may be an additive introduced into the CSF. The additive may bind to or otherwise interact with the target such that when light is applied, the light and/or the additive ultimately causes a change in the target. For example, when the additive is exposed to a particular frequency and/or intensity of light, the additive may release, cause the release of, or accelerate the release of reactive oxygen species (e.g., peroxides, super oxides, etc.). The reactive oxygen species may inactive or otherwise damage the target. Various additives may be used. Some additives may include methylthioninium chloride (methylene blue).

The systems and methods for applying photodynamic therapy may be similar to or the same as systems and methods for applying UV treatment. For example, photodynamic therapy may be applied using UV treatment system 500 using the UV lamp 508 or a different light source. A light source used for photodynamic therapy may be a lamp, laser or another source of electromagnetic radiation. The light source for photodynamic therapy may emit light at various wavelengths, including but not limited to a wavelength selected from the range of about 10 nanometers to about 1 millimeters. For example, the light source may be configured to emit light at a frequency of 660 nanometers.

Increasing CSF Flow Rate or Flow Volume

In typical TFF systems, high fluid flow rate and fluid flow volume is used to prevent membrane clogging and improve TFF performance and longevity. However, withdrawing fluid from and returning fluid to a subject at a high flow rate and high volumes presents challenges. In particular, should something go wrong with the system 100 (e.g., a clog or pinched tubing), high flow rates and high volumes may result in the system's problems quickly affecting the subject. For example, if CSF is withdrawn and returned to the patient at a high rate and there is a clog in the system 100 that prevents the return of CSF to the patient, a large amount of CSF may be withdrawn, causing problematically low levels of CSF within the subject.

Figure 9:
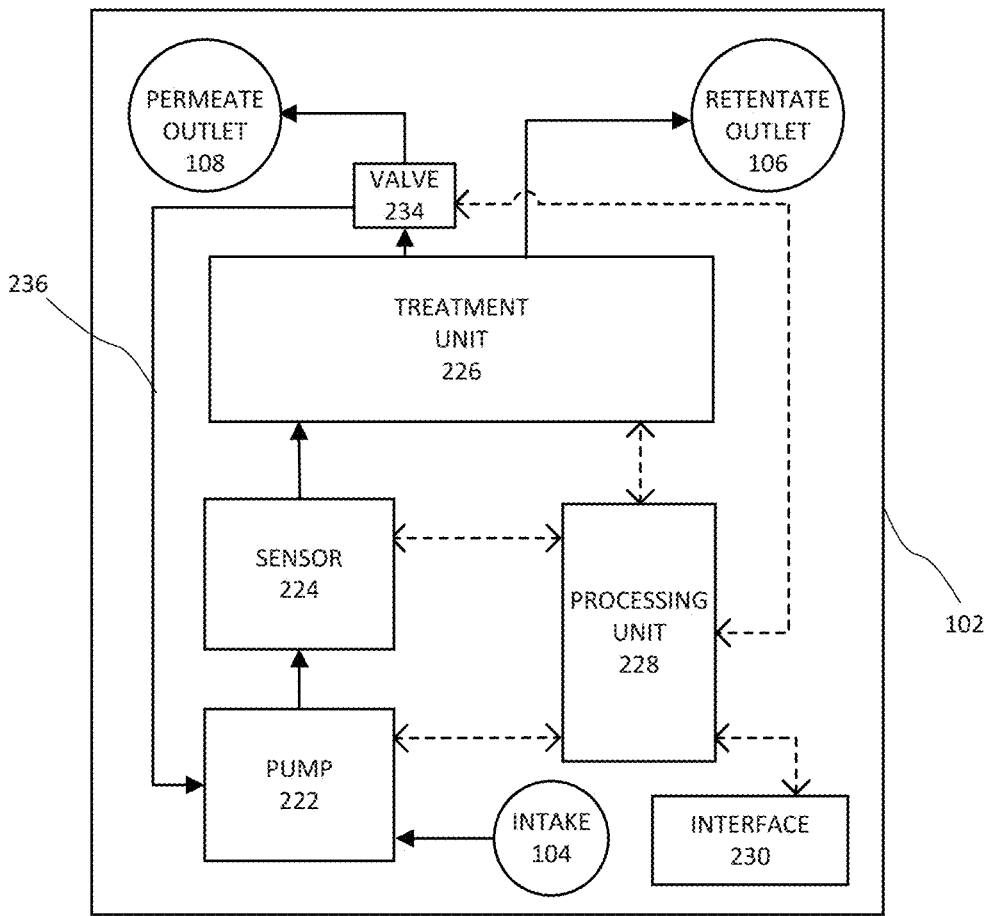
FIG. 9 illustrates an embodiment of a treatment system having a valve and a feedback path to increase fluid flow rate across a filter according to some embodiments.

FIG. 9 illustrates an embodiment of a treatment system 102 having a valve 34 and feedback path 236 to artificially increase fluid flow rate across the treatment unit 226, for example to improve the effectiveness of a TFF of the treatment unit 226. The valve 234 may control the amount of fluid flow heading towards the permeate outlet 108 and through a feedback path 236 towards the pump 222 from the treatment unit 226. Specifically, the valve 234 may restrict the amount of fluid flow back to the subject, thereby increasing the amount of fluid passing back through pump 222 and towards the treatment unit 226. The CSF that flows back through the feedback path 236 through the pump 222 may be used to increase the fluid flow rate across a filter. The processing unit 228 may control the operation of the valve 234 to ensure that the amount of fluid feeding back to the pump 222 is not too high. The total amount of fluid within the feedback path 236 may be controlled, adjusted, or selected to ensure that the amount of fluid within the feedback path is below an amount that may negatively affect the subject (e.g., by causing a spinal headache in the subject).

In some embodiments, an array of micro-sized TFF systems may be used with a splitter. This system may be advantageous because the fluid flow rate may be faster through each of these TFF systems. Back pressure may be controlled across each of the micro-sized TFF systems.

In some embodiments, another liquid (e.g., artificial CSF, saline, or anther liquid) may be added to boost the amount of fluid moving through the treatment unit 226 to increase performance. The additional volume would enable additional fluid to pass through the treatment unit 226, thereby reducing the likelihood of the filter clogging.

In some embodiments, a volume of CSF may be removed from the patient, then no additional CSF is withdrawn or returned. The CSF isolated in the system 100 may then be filtered at a high speed without risk to the subject. Following sufficient processing, the filtered CSF may be returned and a next amount of CSF may be withdrawn.

Separating Cells Via their Dielectric Properties

Dielectrophoresis (DEP) is a technique in which a non-uniform electric field is applied to dielectric particles, thereby causing the particles to experience DEP forces. The way a particle responds to the non-uniform electric field depends on the particle's unique dielectric characteristics, including permittivity, conductivity, and capacitance. DEP may be used to electrically separate cells, particles, or other components of the CSF from each other or from the fluid itself. The non-uniform electric field that drives the particle movement and separation can be generated in various ways, ranging from spatial distortion of the field to different electrode configurations and geometries.

One application of DEP forces is to particles in a fluid flowing through a chamber. By manipulating the forces acting on the particles (e.g., a combination of hydrodynamic lift, sedimentation, and dielectrophoretic forces) through DEP, a system can alter and control the location of the particles in the fluid's velocity profile (speeding up or slowing down) and thus allow for separation from the rest of the fluid and removal of the particles. In addition, if multiple particles with different dielectric properties are present in a fluid, it is possible to separate them such that one type experiences positive DEP forces and the other type experiences negative DEP forces.

Figure 10:
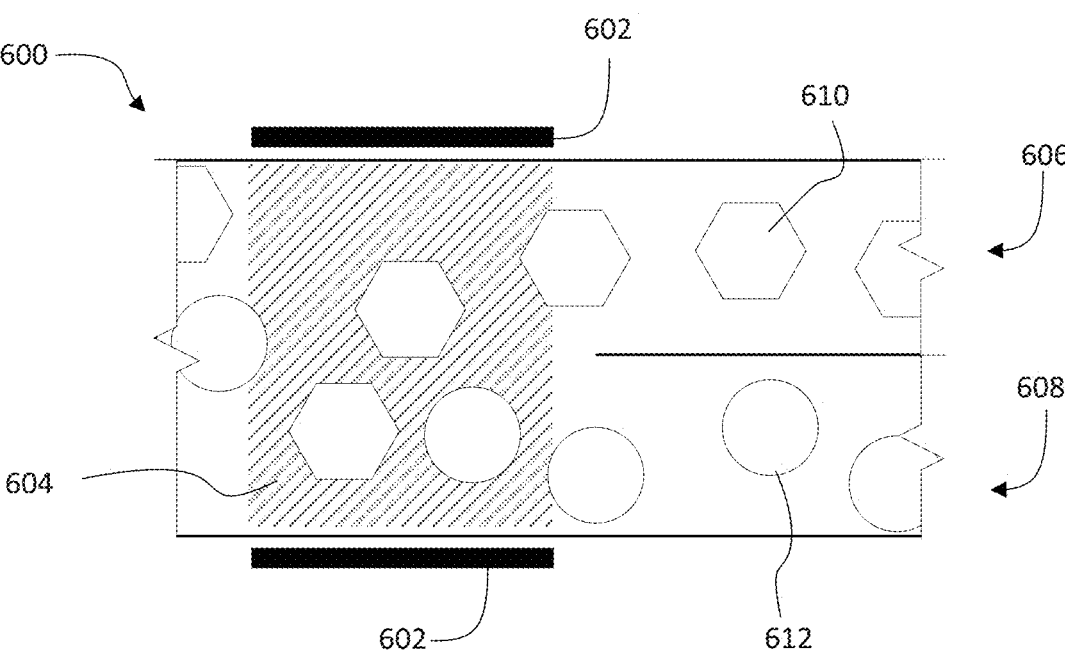
FIG. 10 illustrates a dielectrophoresis system which uses electrodes to create an electric field to direct particles towards particular paths according to some embodiments.

FIG. 10 illustrates an example DEP system 600, which uses electrodes 602 to create an electric field 604 to direct certain particles towards a first path 606 or a second path 608. For example, first particles 610 may be directed to toward the first path 606. Second particles 612 may be directed toward the second path 608 or they may not be encouraged toward a particular path at all.

Because dielectric properties of particles (e.g., dielectric constant/permittivity, conductivity, and membrane capacitance) are dependent on size, structure, and composition, not only do cells have measureable dielectric properties, cells with different phenotypes have differing dielectric properties. Thus, DEP may be used to separate cells, particles, or other biomarkers of interest from each other or from fluid.

Advantageously, DEP separation uses no physical filter and does not have an associated risk of clogging. Additionally, DEP allows for targeted separation by targeting the unique inherent dielectric properties of cells, and can therefore separate different cell types from each other and selectively remove them.

In DEP, a non-uniform electric field is applied to a neutral or charged particle of interest to induce a force. The electric field may be induced using either alternating current or direct current. The magnitude and direction of force experienced by the particle depends on the particle and medium's electrical properties, size, shape, structure, composition of particle, frequency of applied E field, applied voltage, etc. Thus, the force can be manipulated for the desired application. Both positive and negative dielectrophoretic forces ($F_{DEP}$) are possible. A positive $F_{DEP}$ means that the particle is attracted to the high-field regions (local E field maxima), and a negative DEP force means that the particle is attracted to the low-field regions (local E field minima). The determinant of whether the particle will experience a positive or a negative $F_{DEP}$ is the polarizability of the particle compared to the polarizability of the surrounding medium. If the polarizability of the particle is higher than that of the surrounding medium, it has more surface charges and will move toward the high field region (positive DEP force). If the opposite is true, the surrounding fluid will move toward the high field region and the particle will be pushed to the low field region (negative DEP force). $F_{DEP}$ is defined as $$\langle F_{DEP} \rangle = 2\pi r^3 \epsilon_m \text{Re}\left\{ \frac{\epsilon_p^* - \epsilon_m^*}{\epsilon_p^* + 2\epsilon_m^*} \right\} \nabla |\vec{E}_{rms}|^2$$

where εm and $\varepsilon_p$ represent the medium and particle permittivities, respectively, and the term in brackets represents the Claussus Mossoti factor, which represents the relative permittivities of the particle with respect to the suspending medium. The permittivities are modelled as complex functions of the applied electric field, since the complex function allows for both a phase and magnitude (the causal behavior of the permittivity can be modeled as a phase difference), and the real part of this term is used in the $F_{DEP}$ calculation.

The non-uniform electric field can be generated by applying voltage across electrodes of appropriate geometry or by placement of insulators between electrodes to spatially distort the electric field. Geometry of electrodes other than parallel plates may generate non-uniform electric fields, although some geometries are more common than others for both design and efficiency purposes. The electrodes may be arranged in a microelectrode array. The length of the microelectrode array may be selected to optimize separation yields.

DEP may involve the manipulation of forces applied to particles in a fluid flowing through a column. A particle in a flowing fluid experiences a combination of hydrodynamic lift and sedimentation forces, and by applying an external dielectrophoretic force perpendicular to the flow of the fluid, a system can control the position of a particle of interest in a fluid's velocity profile, thus causing it to speed up or slow down since particles at different positions in the fluid's velocity profile travel at different velocities. The can facilitate separation and/or removal.

Differential dielectric affinity separation involves the separation of two different particle types by exploiting differences in the inherent dielectric properties of the two particles. An electric field may be applied such that one of the particle types experiences a positive $F_{DEP}$ while the other experiences a negative, thus separating the particles from each other.

Separation by differential dielectric affinity is affected by the frequency of the applied electric field. When the DEP response is plotted as a function of applied electric field frequency, the crossover frequency is defined as the x-intercept (the frequency at which the $F_{DEP}$=0). When separating two different particles types, the system may be set to a frequency in between the crossover frequency of the two particles, such that one experiences a positive force and the other experiences a negative force.

The separation may cause a target type of particles to travel down a target path. In some embodiments, the target path may be through a porous membrane (e.g., membrane 258) on the sides of a fluid pathway. In particular, the target molecule may be attracted to an electrode on the other side of the membrane. The target particle may be pass through the filter. Once the target particle passes through the membrane, it may be prevented or discouraged from returning to the other side of the membrane.

In some embodiments, the target path may be a particular path at an intersection. For example, there may be a Y-junction in a flow path. The target particles may be pulled in a particular direction, so they are more likely to flow in one direction over another. This filtration may be a statistical process and be performed several times so there is a particular level of filtration (e.g., 99.9% filtration). In this process, there may be separate side loops that work through the separated material at a high rate. In some embodiments, there may be more than two potential flow paths. For example, there may be three different flow paths at a particular junction. The different flow paths may be separated based on the target molecule. In some embodiments, the particular flow paths may be subjected to different levels of treatment.

Many diseases of the central nervous system manifest in the CSF and show CSF dissemination of certain foreign/unwanted matter such as cells, proteins, or other molecules. It would be advantageous to have a method to specifically target and separate these particles from each other or from the fluid itself based on their inherent dielectric characteristics. Some embodiments may be directed to a method of electrical separation that allows for the application of CSF therapeutics to a wider range of central nervous system disease states (other than subarachnoid hemorrhage-induced cerebral vasospasm) that allows for specific targeting and removal without the use of a physical filter.

Examples of targets include leptomeningeal carcinomatosis tumor cells, which may be present in the CSF and resulting from metastases of various cancers. Similarly, glioblastoma, a rapidly-progressing and usually fatal tumor that generally forms in the central hemispheres of the brain and arises from astrocytes, tumor cells may disseminate in the CSF. CSF dissemination occurs in 10-27% of cases of glioblastoma patients. See, e.g., Cerebral Glioblastoma with Cerebrospinal Fluid Dissemination, NEUROSURGERY, vol. 25, issue 4, pp. 533-540 (October 1989), hereby fully incorporated by reference for any and all purposes as if set forth herein in its entirety. The circulation of tumor cells in the CSF pathways can lead to blockages, hydrocephalus, and further spread of cancer. In addition, *Cryptoccocal meningitis*, Alzheimer's, Multiple Sclerosis, and a variety of other central nervous system disease states are associated with CSF biomarkers that are not present in normal CSF. These biomarkers are correlated to the pathology and progression of these diseases. Examples of CSF biomarkers associated with these disease states include fungi, p-tau proteins (hyperphosphorylated tau proteins), B-amyloid deposits, cytokines, B/T cells, autoantibodies, and more. Different proteins may have different dielectric properties. See Jed W. Pitera, et al., Dielectric Properties of Proteins from Simulation: The Effects of Solvent, Ligands, pH, and Temperature, BIOPHYSICAL JOURNAL 80, no. 6 (June 2001): 2546-55. doi:10.1016/S0006-3495(01)76226-1, hereby fully incorporated by reference for any and all purposes as if set forth herein in its entirety. Therefore, DEP-based filtration may be used to target biomarkers associated with a variety of disease states.

Many DEP research studies perform separation experiments in a series of discontinuous steps involving a loading of the suspension step, a washing step, and an elution step. Such discontinuous procedures limit the separation throughput and scaling of the technique and would make integration of the DEP separator with a CSF treatment system difficult. Thus it may be desirable to implement a continuous system. See Ki-Ho Han, et al., Lateral-Driven Continuous Dielectrophoretic Microseparators for Blood Cells Suspended in a Highly Conductive Medium, LAB ON A CHIP 8, no. 7 (Jun. 27, 2008): 1079-86. doi:10.1039/B802321B, hereby fully incorporated by reference for any and all purposes as if set forth herein in its entirety.

The medium in which the target is located is also a factor in applying DEP to CSF. The relative polarizability (which depends on permittivity and conductivity) of the particle with respect to the medium determines whether a particle will experience a positive or negative $F_{DEP}$. A particle that is more polarizable than the surrounding medium will experience a positive DEP force, and vice versa. Most DEP separation studies control the conductivity of the suspension medium to ensure a low conductivity (compared to physiological medium) of about 30-60 mS/m, to optimize parameters for strong positive DEP separation forces. However, controlling the conductivity of the medium is not clinically relevant and a low conductivity suspension medium is not physiologically relevant since physiological fluids usually have higher conductivities (10-100 times higher than mediums used in many DEP experiments). The electrical conductivity of the CSF at body temperature may be approximately 1790 mS/m, which is about two orders of magnitude higher than the conductivity of mediums used in many DEP research studies. Stephen B. Baumann, et al., The Electrical Conductivity of Human Cerebrospinal Fluid at Body Temperature, IEEE TRANSACTIONS ON BIOMEDICAL ENGINEERING 44, no. 3 (March 1997): 220-23. doi: 10.1109/10.554770, hereby fully incorporated by reference for any and all purposes as if set forth herein in its entirety.

Figure 11:
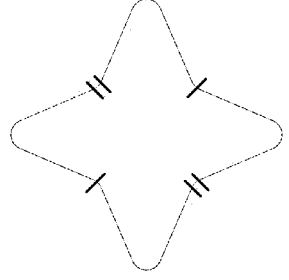
FIG. 11 illustrates a polynomial channel path according to some embodiments.
Figure 12:
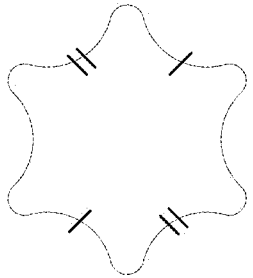
FIG. 12 illustrates a polynomial channel path according to some embodiments.

Most cells in CSF would experience negative DEP forces at a wide range of E field frequencies, because CSF is a highly conductive suspension medium. Ki-Ho Han, et al., Lateral-Driven Continuous Dielectrophoretic Microseparators for Blood Cells Suspended in a Highly Conductive Medium, LAB ON A CHIP 8, no. 7 (Jun. 27, 2008): 1079-86. doi:10.1039/B802321B, hereby fully incorporated by reference for any and all purposes as if set forth herein in its entirety. This presents a challenge for trapping and removing particles, but electrode channel design may be used to address this challenge. Studies have used electrodes of polynomial geometry constructed using photolithography for directing and collecting yeast cells away from electrode edges. Y. Huang, et al., Electrode Design for Negative Dielectrophoresis, MEASUREMENT SCIENCE AND TECHNOLOGY 2, no. 12 (Dec. 1, 1991): 1142-46. doi:10.1088/0957-0233/2/12/005, hereby fully incorporated by reference for any and all purposes as if set forth herein in its entirety. Potential application of this system would be trapping or suspending the cells of interest in a certain area and then washing them away via a separate flow loop or channel. FIGS. 11 and 12 illustrate embodiments of polynomial channel paths, with single and double dash marks on paths indicating differences in electrical polarity on a given curve.

DEP separators may be scaled to handle larger volumes of fluid; however, many DEP separators used in research studies are limited to microfluidics applications with low throughput. The main reason for this is that electric field intensity decays exponentially with increasing distance from electrodes, and $F_{DEP}$ is proportional to the electric field intensity. Studies using planar microelectrode arrays, which usually lie at the bottom of the chamber, are limited in column height and thus volume of fluid they can process because the E field is inversely proportional to the square of the distance from electrodes; a particle in the fluid towards top of chamber (farther away from the electrodes) may not be exposed to the E field, or may not be exposed to enough E field for it to experience an appreciable force necessary for separation.

A potential solution to this is the use of 3D microelectrode array (MEA) designs. As opposed to a planar microelectrode array resting on the bottom of the column, 3D MEAs would extend the E field further up into fluid, allowing particles in all locations of the fluid's velocity profile to experience an appreciable dielectrophoretic force. 3D microelectrodes may affect the fluid's velocity profile. The fluid's velocity profile can be modeled using Navier-Stokes equations and finite-element analysis.

Studies have proposed the use of carbon microfabrication techniques to correlate the electric field distribution with the velocity profile of the fluid. Benjamin Y. Park, et al., 3-D Electrode Designs for Flow-through Dielectrophoretic Systems, ELECTROPHORESIS 26, no. 19 (October 2005): 3745-57. doi:10.1002/elps.200500138, hereby fully incorporated by reference for any and all purposes as if set forth herein in its entirety. In some embodiments, if a particle experiences negative DEP force under the experimental conditions, it will be attracted to low field regions, thus it may be advantageous to have higher flow rates in these regions to promote separation and removal. Accordingly, the electrode geometry may be designed such that low field regions coincide with high velocity regions in the fluid's velocity profile.

Options for 3D electrode design include extensions of 2D designs, or other designs. FIGS. 13-15 illustrate some example designs. Benjamin Y. Park, et al., 3-D Electrode Designs for Flow-through Dielectrophoretic Systems, ELECTROPHORESIS 26, no. 19 (October 2005): 3745-57. doi: 10.1002/elps.200500138, hereby fully incorporated by reference for any and all purposes as if set forth herein in its entirety. FIG. 13 illustrates a DEP system 600 having 3D cylindrical electrodes 602 having a diameter of 10 μm, a center to center distance of 20 μm. Voltages of +/−1V may be applied to the electrodes 602, with the voltage on each electrode 602 is opposite in polarity to the adjacent electrodes). FIG. 14 illustrates a DEP system 600 having 3D castellated electrodes 602 having a length of, 5 μm. Voltages of +/−5V may be applied to the electrodes. The voltage on each electrode 602 may be opposite in polarity to the adjacent electrodes 602. FIG. 15 illustrates a DEP system 600 having 3D semi-circular electrode design with long, semi cylindrical electrodes 602 places near each other. The electrodes 602 may be approximately 400 μm in diameter with 100 μm distance between electrodes 602. Voltages of +/−5V may be applied to the electrodes. In some embodiments, there may be closely-spaced wire electrodes being 1.58 mm in diameter, and having spacing between electrodes of about 250 μm with a channel that is approximately 2 mm in height). In some embodiments, multiple arrays of electrodes can be stacked for increased throughput. In addition, it is also possible to line both the top and bottom of the chamber with microelectrodes, thus creating a paired microelectrode multi-layered structure within the microchannel. D. Chen, et al., A 3D Paired Microelectrode Array for Accumulation and Separation of Microparticles, J. OF MICROMECHANICS AND MICROENGINEERING 16, no. 7 (Jul. 1, 2006): 1162. doi:10.1088/0960-1317/16/7/008, hereby fully incorporated by reference for any and all purposes as if set forth herein in its entirety. For example, this design may generate dielectrophoretic gates between the top and bottom electrodes with high-frequency AC voltage. Variables such as channel height, particle size and dielectric characteristics, electrode width and spacing, and more determine whether the particle settles near the gates or penetrate the gates.

A potential advantage of electrical separation is that since there is no use of a physical filter, there is reduced risk of clogging and the filtration is not limited by the size of the particles of interest. For example, consider a situation in which it was desirable to separate two particles of the same size/mass from each other, or if multiple particles of the same size/mass were present in the fluid and it was desirable to only remove one type of particle from the fluid. In either of these cases, electrical separation could be an option for purification since size/mass-based filtration would not be applicable.

Because DEP exploits inherent dielectric characteristic differences between cells of differing phenotypes, it has the potential to be broadly applicable to a range of central nervous system disease states.

There may be challenges associated with this technique. For example, electrode surfaces may become saturated with cells after a period of time (e.g., approximately 30 minutes). In general, if the concentration of the target particle in the fluid is too high, the electrode surfaces and/or areas where particles are being collected may become saturated after a certain period of time. This would result in a decrease in separation efficiency and cells would cease being separated from the fluid (e.g., CSF would mostly likely just continue being circulated as opposed to circulated and purified). Thus, the concentration of the target molecule in the CSF may be a consideration.

In some embodiments, a method for treating the CSF with dielectric separation may involve withdrawing a volume of CSF and encouraging target molecules to flow in a particular direction or along a specific path by inducing an electric field through the CSF. Withdrawing the CSF may be performed according to various methods and systems described herein.

In some embodiments, a method for treating the CSF with dielectric separation may involve withdrawing a volume of CSF, capturing target molecules (e.g., at electrode surfaces or in collection wells) by applying an electric field to the CSF, and returning the processed CSF to the subject.

Applying Spiral and/or Centrifugal Separation

Figure 16:
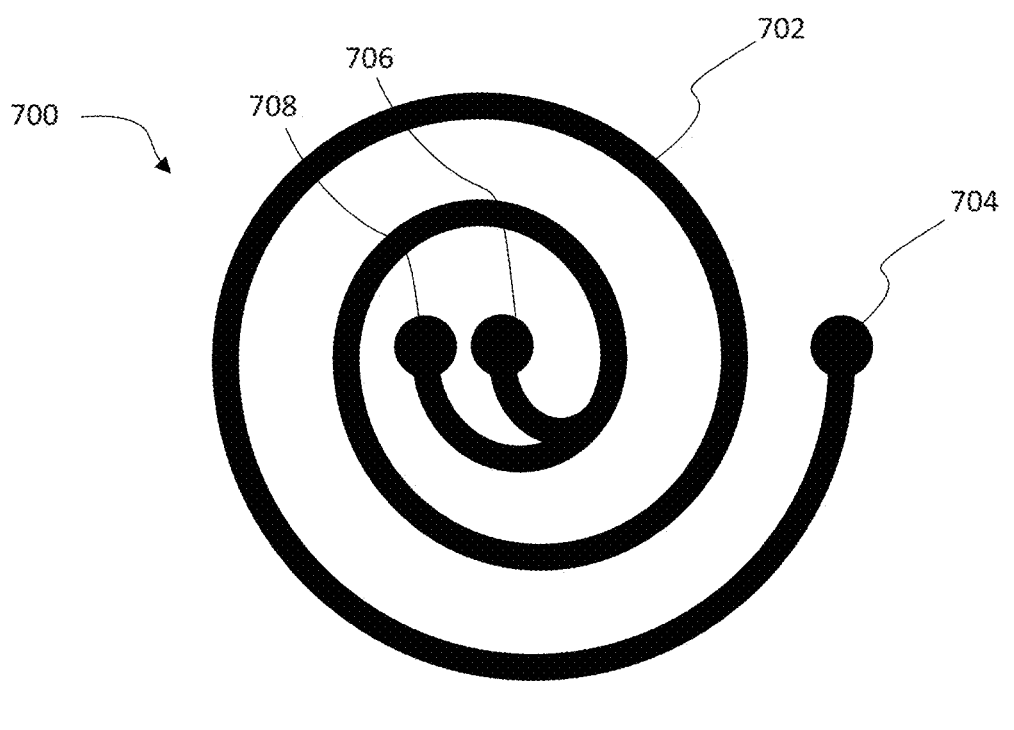
FIG. 16 illustrates systems and methods for using spiral or centrifugal separation according to some embodiments.
Figure 17:
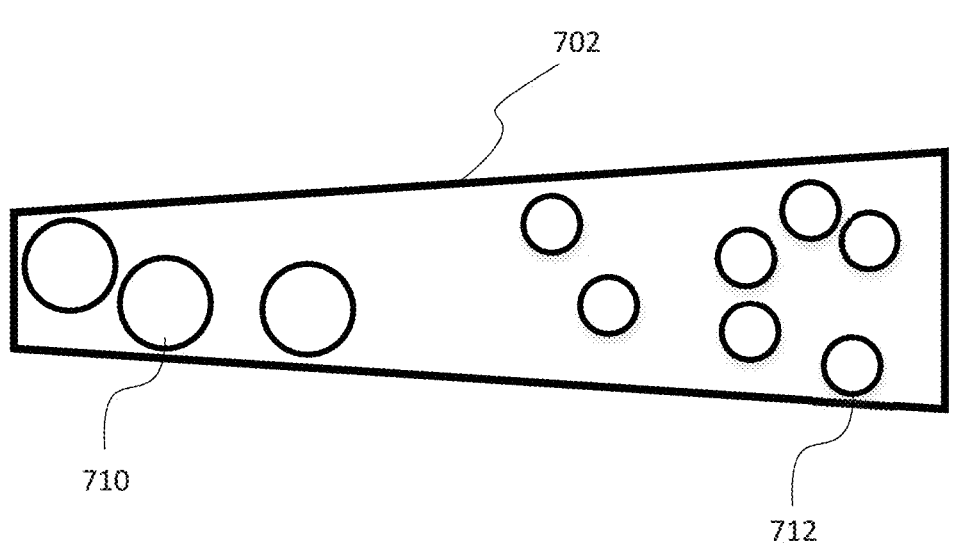
FIG. 17 illustrates a cross section of a path of a spiral or centrifugal separation system according to some embodiments.

FIG. 16 illustrates systems and methods for using spiral and/or centrifugal separation (with or without recombination) by mass separate targets from CSF, including a centrifugal separation system 700. In particular, the system 700 may include a path 702 connecting an intake 704 to a first outlet 706 and a second outlet 708. The path 702 follows a spiral pattern from the intake 704 to the first and second outlets 706, 708. FIG. 17 illustrates a cross section of the path 702. The path may have a trapezoidal cross section. As first particles 710 and second particles 712 travel through the path 702, centrifugal forces imparted on the particles 710, 712 by the spiral path may cause heavier particles (e.g., first particles 710) to gather at one end of the cross section and lighter particles to gather at the opposite end of the cross section. The fork that leads to the first and second outlets 706, 708 may be configured to use this tendency to gather to separate the particles, such that the first particles 710 generally travel toward the first outlet 706 and the second particles 712 generally travel towards the second outlet 708. In embodiments where the targets are separated by mass, some molecules may be recombined and others may be excluded so as to function as a notch or bandpass filter in the mass. In some embodiments, a hydrocyclone may be used. A hydrocyclone may apply centrifugal force to the CSF encouraging the separation of components of the CSF based on their mass.

In some embodiments, a method for applying spiral and/or centrifugal separation may include withdrawing a volume of CSF, passing the volume of CSF through a hydrocyclone to separate the CSF into first and second volumes, and returning one of the first or second volumes to the subject. Withdrawing and returning the CSF may be performed according to various methods and systems described herein.

Binding Additives to Target Molecules

Some systems and methods may involve introducing an additive into the CSF. This step may include directly introducing the additive into the treatment site 112 (e.g., via port 124) or by other means (e.g., such as an orally-administered substance). In some embodiments, the additive is added to the CSF after the CSF has been removed from the treatment site 112. The additive may serve various purposes, including but not limited to improving the effectiveness of the treatment system 102 (e.g., by making a material more easily filtered-out by a filter of the treatment system 102), increasing the safety of the procedure, improving the health of the patient, or other purposes. For example, in certain embodiments, the additive may be a binding drug, molecule, salt, or other binding material. The binding additive may preferentially bind to certain target materials within the CSF to modify how the material interacts with the treatment system 102.

For example, in certain embodiments, the binding additive may preferentially bind to a target material (e.g., a protein or cytokine), causing the target to become larger in size or precipitate out, thereby making the target more easily removed by a filter of the treatment system 102. In certain embodiments, the additive may be configured to change a dielectric property of the target to make the target more or less easily filtered by a filter of the treatment system 102. In certain embodiments, the additive is given a particular amount of time to work or otherwise interact with target before a next step is taken. For example, there may be a waiting period after the additive has been introduced to the CSF to give the additive time to bind with or otherwise modify the target before the CSF is filtered or otherwise processed.

In some embodiments, an additive has specific properties (e.g., size, mass, dielectric constant, magnetism, etc.), which may be used to target particular targets (e.g., by chemically or biologically targeting a protein or some other tag). The additive molecules may attach to the target particle, so the target particle is more easily separable from the CSF. For example, the additive molecule may make the particle of interest larger so the additive-target combination may be more easily separated by size-exclusion filtration. The additive-target combination may be heavier to encourage separation by centrifugal filtration (e.g., as described above). The additive-target combination may have altered dielectric properties, making it more easily separable using the dielectric separation method.

As a particular example, a health care professional may desire to a remove a target protein, and introduce a gold micro or nano particle additive to the CSF. The additive may have a tag (e.g., a chemical tag) for the target. The additive may then attach to the target, making the additive-target combination larger or otherwise more easily filtered. The now-larger additive-target combination is then more easily removed.

In some embodiments, a treatment system 102 may include a pre-mixing system in which the additive is mixed with the CSF. The pre-mixing system may be configured to cause the additive to mix with the CSF and react with the target. The pre-mixing system may be configured with particular parameters, such as a particular temperature, pressure, or other conditions. The pre-mixing system may be configured such that the additive is allowed to react with the target for a particular amount of time before the CSF leaves the system. The additive-target combination may then move through the system and eventually be filtered out (e.g., using a dead end filter).

In some embodiments, the separated additive-target combination is deposited into a waste bag. The additive-target combination may be separated from the CSF in the waste bag (e.g., because the additive-target combination sank to the bottom of the waste bag) and the CSF in the waste bag may be recycled into the system 100. For example, the CSF may be added back to an inflow of the treatment system 102 and processed again.

In some embodiments, the additive includes magnetic nanobeads configured to capture particular molecules, pathogens, germs, toxins, or other targets. For example, the magnetic nanobeads may be coated with engineered human opsonin (mannose-binding lectin), which may capture a wide variety of targets. Once the additive binds to the target, the additive-target combination may be separated from the CSF using a magnet.

Combined Systems

In some embodiments, there may be multiple divided subloops (in parallel or series) that have different treatments and are recombined as necessary. The different loops may enable different treatment. For example, one loop may be con figured to use UV light to kill bacteria and then the fluid passes through a different subloop configured to heat the fluid to slow reproduction of fungus and then cooling the CSF before it is returned to the subject. In some embodiments, vibrating the treatment unit 226 may discourage clogging, coagulating, clotting, and settling on the treatment unit 226.

Multiple systems may be used to provide incremental enhancements to the CSF prior to filtration. For example, filtering using a hydrocyclone and dielectric separation techniques may remove a percentage of the target molecules, with the remaining amount removed by a TFF system. While not necessarily removing the need for a filtering system, the hydrocyclone and dielectric separation may remove an amount of target (or other) particles to improve performance of a treatment system.

Targets

The targets may be any kind of biomarker, the removal of which is or may be associated with particular health outcomes for the subject. In some embodiments, the target may be an organism known to or thought to cause a particular disease or health condition, such as meningitis. In some embodiments, the targets may be metastases. In some embodiments, the target may be polysaccharide capsules. For example, some germs, such as *Cryptococcus* and *Neisseria meningitides*, are encapsulated in a polysaccharide capsule. After the germ sheds the capsule, the capsule may be suspended within the CSF. Both the germ and the capsule may be targeted for removal. While the germ may be a primary target, the capsule is relatively large and may problematically cause clogging in some filters. As another example, glial fibrillary acid proteins may be targeted. These proteins may be a marker for astrocytic differentiation in patients with cerebral glioblastoma. Other markers of CSF dissemination of glioblastoma may also be removed.

There are a number of cytokines that have been implicated in inflammation in acute brain injury and chronic brain injury, which may also be a target. Similar to other disease processes, the early stage of inflammation can facilitate healing but inflammation that increases over time and becomes "chronic" can have severe long-term effects on cognition and overall mental health.

Embodiments may enable filtration of cytokines like TNF-$\alpha$, interleukins and other cytokines from the CSF of a compromised brain. By actively decreasing the cytokine load, during a chronic inflammation, overall brain health would improve significantly. Removal of substances in the 25 kDa to 80 kDA range would be important to protect on the filtration side.

Examples of cytokines and other proteins that may be targeted may include, but need to be limited to, EGF, Eotaxin, E-selectin, fas ligand, FGF2, Flt3 lig, fractalkine, G-CSF, GM-CSF, GRO, ICAM, IFNa2, IFNg, IL10, IL12p40, IL12p70, IL13, IL15, IL17, IL1a, IL1b, IL1ra, IL2, IL3, IL4, ILS, IL6, IL7, IL8, IL9, integrins, IP10, L-selectin, MCP1, MCP3, MDC, MIP1a, MIP1b, PDGF-AA, PDGF-AAAB, P-selectin, RANTES, sCD40L, sIL2R, TGFa, TNF, TNFb, VCAM, VEGF, and others. In some embodiments, the treatment unit 226 may be configured to capture and absorb cytokines in the about 10 to about 50 kDa range where most cytokines reside.

Various journal articles and other publications are cited in this disclosure. Each of those is hereby incorporated by reference herein for any and all purposes, as if fully set forth herein.

Within this disclosure, connection references (for example, attached, coupled, connected, and joined) may include intermediate members between a collection of components and relative movement between components. Such references do not necessarily infer that two components are directly connected and in fixed relation to each other. The exemplary drawings are for purposes of illustration only and the dimensions, positions, order and relative sizes reflected in the drawings attached hereto may vary.

The above specification provides a complete description of the structure and use of exemplary embodiments as claimed below. Although various embodiments of the invention as claimed have been described above with a certain degree of particularity, or with reference to one or more individual embodiments, those skilled in the art could make numerous alterations to the disclosed embodiments without departing from the spirit or scope of this disclosure. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the disclosure as defined in the following claims.

What is claimed is:

1. A system for treating cerebrospinal fluid, comprising:
   a catheter assembly coupled a first fluid pathway for transporting a volume of cerebrospinal fluid from a patient to a filter and a second fluid pathway for returning filtered cerebrospinal fluid back to the patient;
   a pump configured to withdraw the volume of cerebrospinal fluid from the patient and transfer the volume of cerebrospinal fluid to the filter along the first fluid pathway;
   wherein the filter is configured to separate the volume of cerebrospinal fluid into a permeate and a retentate;
   wherein the filter is configured to remove a target microorganism from the volume of cerebrospinal fluid such that the permeate is substantially free of the target microorganism; and
   wherein the pump is configured to return at least a portion of the permeate to the patient along the second fluid pathway.

2. The system of claim 1, wherein the filter includes a tangential flow filter.

3. The system of claim 1, further comprising a sensor disposed adjacent to the filter.

4. The system of claim 3, wherein the sensor is configured to measure a characteristic of the volume of cerebrospinal fluid.

5. The system of claim 4, wherein the characteristic is a difference between a first flow rate along the first fluid pathway and a second flow rate along the second fluid pathway.

6. The system of claim 4, wherein the characteristic is a difference between a first fluid volume along the first fluid pathway and a second fluid volume along the second fluid pathway.

7. The system of claim 4, further comprising a processing unit coupled to the catheter assembly, the processing using being configured to increase a rate at which the volume of cerebrospinal fluid passes through the filter by diverting a diverted portion of the permeate or the retentate back through the filter.

8. The system of claim 7, wherein the processing unit is configured to update a parameter of a set of operation parameters based on the measured characteristic responsive to determining that the measured characteristic passes a predetermined threshold.

9. The system of claim 1, wherein the pump is configured to withdraw the volume of cerebrospinal fluid from the patient at a first flow rate and the pump is configured to return at least the portion of the permeate to the patient at a second flow rate different from the first flow rate.

10. The system of claim 1, further comprising an inactivating member coupled to the filter.

11. The system of claim 10, wherein the inactivating member includes a heating member.

12. The system of claim 10, wherein the inactivating member includes a cooling member.

13. The system of claim 10, wherein the inactivating member includes an ultraviolet radiation member.

14. The system of claim 1, wherein the target microorganism is a meningitis-related microorganism.

15. A system for removing a target microorganism from cerebrospinal fluid, comprising:
   a catheter assembly coupled a first fluid pathway and a second fluid pathway t;
   a filter coupled to the catheter assembly;

wherein the filter is configured to separate a volume of cerebrospinal fluid withdrawing from a patient into a permeate and a retentate;
   wherein the filter is configured to remove the target microorganism from the volume of cerebrospinal fluid; and
   a pump configured to withdraw the volume of cerebrospinal fluid from the patient and transfer the volume of cerebrospinal fluid to the filter along the first fluid pathway and return at least a portion of the permeate to the patient along the second fluid pathway.

16. The system of claim 15, wherein the filter includes a tangential flow filter.

17. The system of claim 15, further comprising an inactivating member coupled to the filter.

18. The system of claim 17, wherein the inactivating member includes a heating member, a cooling member, an ultraviolet radiation member, or combinations thereof.

19. The system of claim 15, wherein the target microorganism is a meningitis-related microorganism.

20. A system for treating cerebrospinal fluid, comprising:
   a catheter assembly coupled a first fluid pathway for transporting a volume of cerebrospinal fluid from a patient to a filtration system coupled to the catheter assembly and a second fluid pathway for returning filtered cerebrospinal fluid back to the patient;
   wherein the filtration system includes one or more tangential flow filters;
   a pump configured to withdraw the volume of cerebrospinal fluid from the patient and transfer the volume of cerebrospinal fluid to the filtration system along the first fluid pathway;
   wherein the filtration system is configured to separate the volume of cerebrospinal fluid into a permeate and a retentate;
   wherein the filtration system is configured to remove a meningitis-related microorganism from the volume of cerebrospinal fluid; and
   wherein the pump is configured the return the permeate to the patient along the second fluid pathway.

* * * * *